United States Patent
Lin

(10) Patent No.: US 10,773,018 B2
(45) Date of Patent: Sep. 15, 2020

(54) SAFETY MECHANISM FOR A RETAINING NEEDLE AND A RETAINING NEEDLE HAVING THE SAFETY MECHANISM

(71) Applicant: SOL-MILLENNIUM MEDICAL HK LIMITED, Hong Kong (CN)

(72) Inventor: Zuoqian Lin, Zhejiang (CN)

(73) Assignee: SOL-MILLENNIUM MEDICAL HK LIMITED, Hong Kong (CN)

( * ) Notice: Subject to any disclaimer, the term of this patent is extended or adjusted under 35 U.S.C. 154(b) by 336 days.

(21) Appl. No.: 15/580,461

(22) PCT Filed: Jun. 24, 2016

(86) PCT No.: PCT/CN2016/087002
§ 371 (c)(1),
(2) Date: Dec. 7, 2017

(87) PCT Pub. No.: WO2016/206624
PCT Pub. Date: Dec. 29, 2016

(65) Prior Publication Data
US 2018/0318500 A1    Nov. 8, 2018

(30) Foreign Application Priority Data
Jun. 25, 2015    (CN) .................... 2015 2 0454957 U

(51) Int. Cl.
*A61M 5/158*    (2006.01)
*A61M 25/06*    (2006.01)
*A61M 5/32*    (2006.01)

(52) U.S. Cl.
CPC ........ *A61M 5/158* (2013.01); *A61M 25/0631* (2013.01); *A61M 25/0606* (2013.01);
(Continued)

(58) Field of Classification Search
CPC .......... A61M 25/0631; A61M 25/0612; A61M 2005/3242; A61M 25/0606; A61M 25/0637
See application file for complete search history.

(56) References Cited

U.S. PATENT DOCUMENTS 5,480,385 A    1/1996  Thorne et al.
5,487,734 A    1/1996  Thorne et al.
(Continued)

FOREIGN PATENT DOCUMENTS

CN    1171745 A    1/1998
CN    1277874 A    12/2000
(Continued)

OTHER PUBLICATIONS

Translation of and original International Search Report and original Written Opinion dated Sep. 1, 2016 in counterpart International Application No. PCT/CN2016/087002, 17 pps.

*Primary Examiner* — Emily L Schmidt
(74) *Attorney, Agent, or Firm* — Shumaker & Sieffert, P.A.

(57) ABSTRACT

The present utility model discloses a safety mechanism for a retaining needle and a retaining needle having the safety mechanism. The retaining needle comprises a hollow handle and a needle seat at least partially disposed within the handle for receiving a puncture needle, the safety mechanism comprises: a snapping step disposed at an inner side of the hollow handle; at least one elastic arm radially spreading outward disposed on the needle seat, an end portion of the elastic arm has a snapping portion radially protruding outward, the snapping portion being engaged with the snapping step; a button disposed on a distal side portion of the handle; the button, when being depressed, pushing the elastic arm along a radial inward direction, such that while the snapping portion of the elastic arm is disengaged from the snapping (Continued)

step, the needle seat and the puncture needle stretching outside of the handle are retracted into the hollow handle by virtue of vacuum within the hollow handle.

13 Claims, 50 Drawing Sheets

(52) U.S. Cl.
CPC . *A61M 25/0612* (2013.01); *A61M 2005/1585* (2013.01); *A61M 2005/1586* (2013.01); *A61M 2005/3242* (2013.01)

(56) References Cited

U.S. PATENT DOCUMENTS

| | | |
|---|---|---|
| 5,542,927 A | 8/1996 | Thorne et al. |
| 5,549,708 A | 8/1996 | Thorne et al. |
| 5,616,135 A | 4/1997 | Thorne et al. |
| 5,656,031 A | 8/1997 | Thorne et al. |
| 5,672,161 A | 9/1997 | Allen et al. |
| 5,823,997 A | 10/1998 | Thorne et al. |
| 5,836,917 A | 11/1998 | Thorne et al. |
| 5,928,200 A | 7/1999 | Thorne et al. |
| 5,980,488 A | 11/1999 | Thorne et al. |
| 6,015,397 A | 1/2000 | Elson et al. |
| 6,024,727 A | 2/2000 | Thorne et al. |
| 6,086,563 A * | 7/2000 | Moulton ........... A61M 25/0631 604/164.01 |
| 8,845,585 B2 | 9/2014 | Wang et al. |
| 2007/0073237 A1 | 3/2007 | Rodd |
| 2017/0216534 A1 | 8/2017 | Kawabe et al. |
| 2019/0255259 A1 | 8/2019 | Lin |

FOREIGN PATENT DOCUMENTS

| | | |
|---|---|---|
| CN | 1803209 A | 7/2006 |
| CN | 103239775 A | 8/2013 |
| CN | 205041892 U | 2/2016 |
| CN | 106237454 A | 12/2016 |
| EP | 2070559 A1 | 6/2009 |
| WO | 2016021323 A1 | 2/2016 |

* cited by examiner

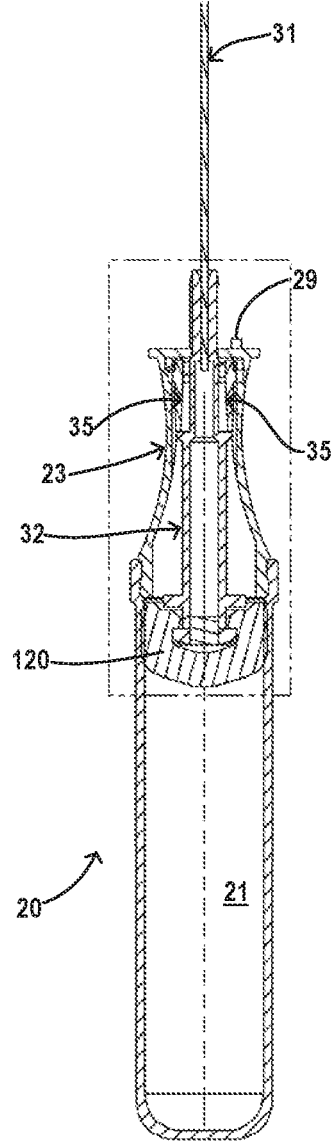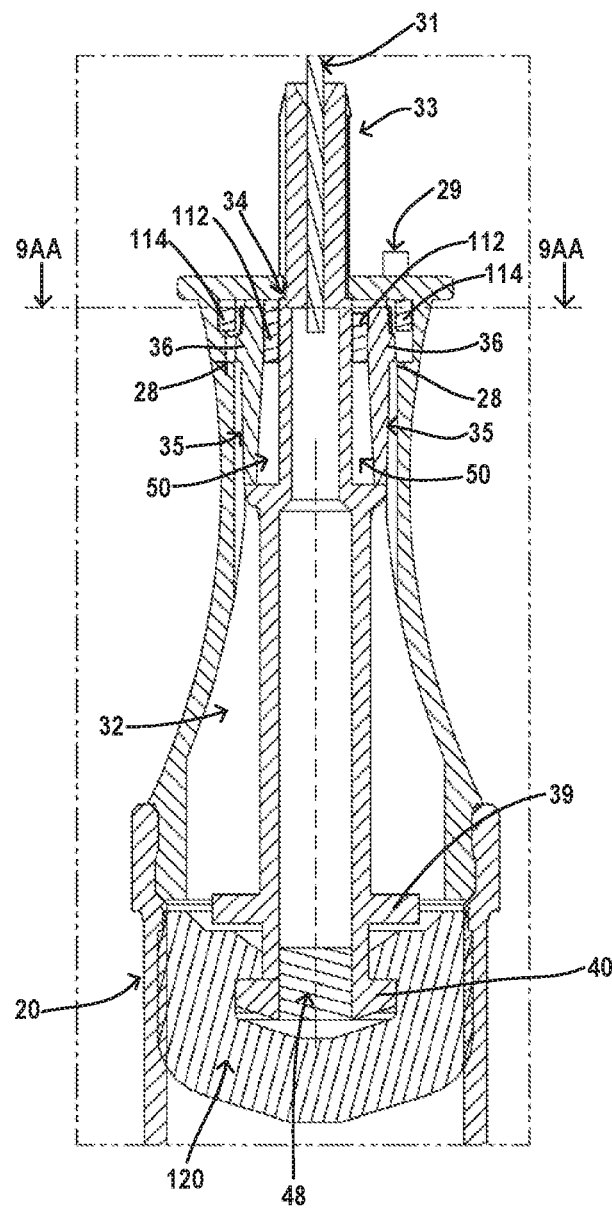
Fig. 10B                    Fig. 10C

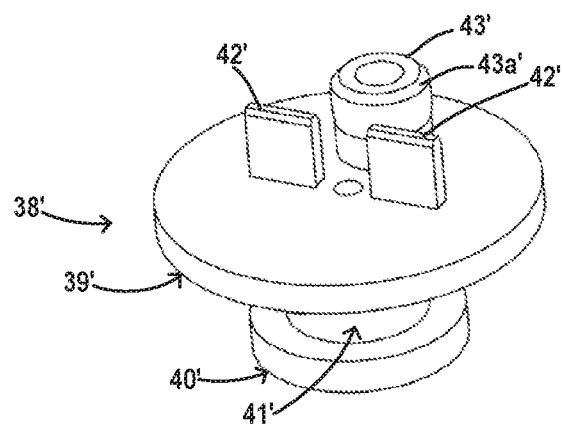
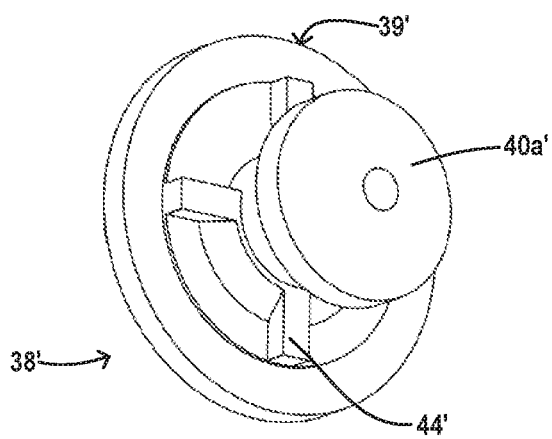
Fig. 15A                    Fig. 15B
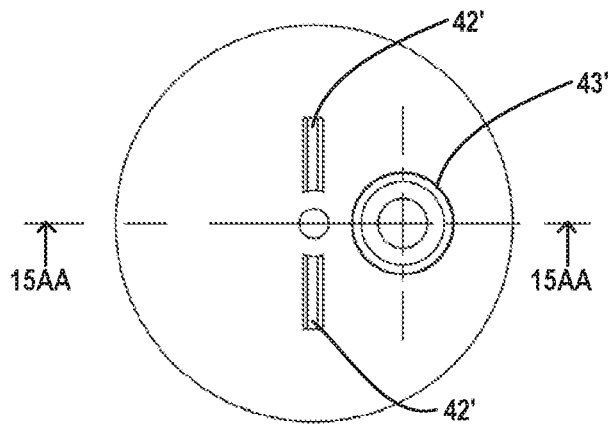
Fig. 15C
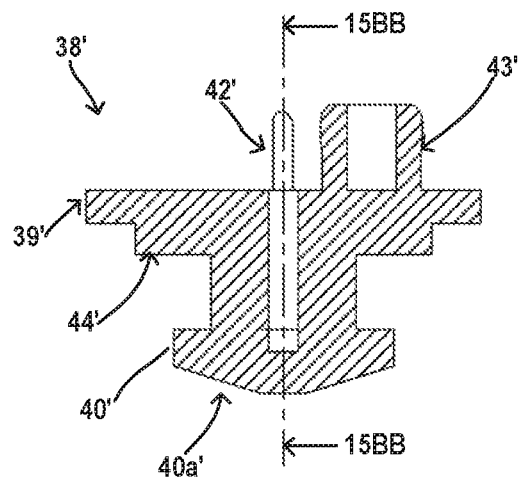
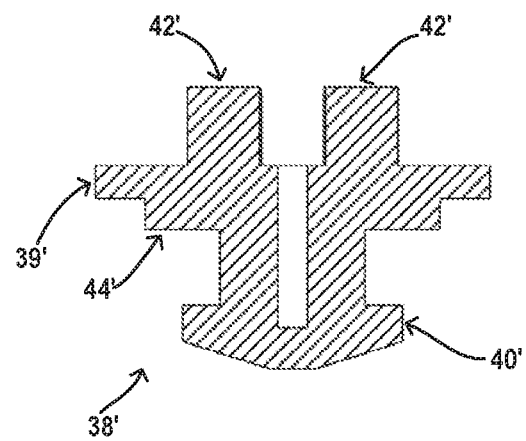
Fig. 15D                    Fig. 15E

SAFETY MECHANISM FOR A RETAINING NEEDLE AND A RETAINING NEEDLE HAVING THE SAFETY MECHANISM

This application is a U.S. national phase application under 37 U.S.C. § 371 of international application number PCT/CN2016/087002 filed on Jun. 24, 2016, which claims the benefit of priority to CN application number 201520454957.3 filed Jun. 25, 2015. The entire contents of each of international application number PCT/CN2016/087002 and CN application number 201520454957.3 are incorporated herein by reference.

FIELD OF THE INVENTION

The present disclosure el relates to a safety mechanism for a retaining needle and a retaining needle having the safety mechanism.

BACKGROUND OF THE INVENTION

With the development of modern medicine, researchers have been devoted to reduce pains brought by medical treatments. Use of intravenous retaining needles (also referred to intravenous trocar) can reduce pains caused by repetitive venipuncture to patients and alleviate workload of healthcare workers, which currently has gained wide application. The existing retaining needles generally comprise a puncture needle and a catheter retained in a blood vessel. During use, the catheter is pierced into the blood vessel with the puncture needle; when the catheter completely enters into the blood vessel, the puncture needle is retracted, only retaining the catheter within the blood vessel, prepared for subsequent treatment.

During use, positioning of the retaining needle is very important. After the puncture needle is penetrated into the patient's blood vessel, the blood pressure of the patient will cause a little blood to flow into the hollow puncture needle, such that when the user observes the little blood at a rear part of the puncture needle, it can be determined that the retaining needle is completely positioned and may be retracted. However, the blood-tainted puncture needle will bring many risks to the healthcare workers and other persons who possibly contact medical garbage, such as infection with diseases, etc.

Currently, puncture-proof retaining needles have emerged in markets, but most of them have a complex structure and a high manufacturing cost; therefore, the price is dear, while the operation is inconvenient.

Accordingly, a retaining needle featuring a high safety, a simple structure, cost-effectiveness, and an easy manipulation and a safety mechanism suitable for the retaining needle for guaranteeing its safety are still desirable.

SUMMARY OF THE INVENTION

The present disclosure provides a safety mechanism for a retaining needle and a retaining needle having the safety mechanism, which safety mechanism allows a safer retraction of the puncture needle after a catheter and a puncture needle of the retaining needle are correctly penetrated into the blood vessel, which avoids a user from contacting the used punctured needle again; therefore, it has a high safety, a simple structure, and cost-effectiveness.

According to one aspect of the present disclosure, there is provided a safety mechanism for a retaining needle, the retaining needle comprising a hollow handle and a needle seat at least partially disposed within the handle for receiving a puncture needle, the safety mechanism comprising: a snapping step disposed at an inner side of the hollow handle; at least one elastic arm radially spreading outward disposed on the needle seat, an end portion of the elastic arm has a snapping portion radially protruding outward, the snapping portion being engaged with the snapping step; a button disposed on a distal side portion of the handle; the button, when being depressed, pushing the elastic arm along a radial inward direction, such that while the snapping portion of the elastic arm is disengaged from the snapping step, the needle seat and the puncture needle stretching outside of the handle are retracted into the hollow handle by virtue of vacuum absorption within the hollow handle.

In one embodiment, the snapping step is disposed on an inner wall at the distal side portion of the hollow handle, and the elastic arm spreading outward radially and extending to a distal direction from a proximal side of the needle seat.

In one embodiment, the button comprises a pressing portion and at least one extruding arm radially extending from the pressing portion, an end of the extruding arm having a thickened part; when the button is not depressed, the extruding arm reaching into a gap between a body of the needle seat and an elastic arm spreading outward radially from the body, and presses the elastic arm against the snapping step using the thickened portion; after the button is depressed, the thickened portion of the extruding arm extends beyond the gap, not radially extruding the elastic arm outwardly anymore.

In one embodiment, the button further comprises at least one driving arm extending radially from the pressing part, the driving arm has an inclined end and is disposed at an exterior side of the extruding arm; when the button is not depressed, the driving arm is disposed external to an end head of the elastic arm without contacting therewith; after the button is depressed, as the thickened portion of the extruding arm reaches beyond the gap so as not to extrude the elastic arm outward radially, an inclined side of the inclined end of the driving arm disposed exteriorly gradually extrudes the elastic arm radially inwardly.

In one embodiment, a width of an end head of the elastic arm is less than a width of a body portion of the elastic arm.

In one embodiment, the button has at least one driving arm extending radially, the driving arm has an inclined end and is disposed at an external side of the elastic arm; after the button is depressed, an inclined side of the inclined end of the driving arm gradually extrudes the elastic arm radially inwardly.

In one embodiment, there are two elastic arms; there is one or two driving arms. In one embodiment, the snapping step is disposed on an inner wall at the distal side portion of the hollow handle, the elastic arm spreading outward radially and extending towards a proximal direction from a distal side of the needle seat.

In one embodiment, the button has at least one driving arm extending radially, the driving arm having an inclined end and being disposed at an external side of the elastic arm; after the button is depressed, an inclined side of the inclined end of the driving arm gradually extrudes the elastic arm radially inwardly.

In one embodiment, there are two driving arms.

In one embodiment, the hollow handle comprises a cylindrical snap sleeve disposed inside the hollow handle; an edge of the snap sleeve extends to a distal side portion of the handle and the edge forms the snapping step, the elastic arm spreads radially outward and extends to a proximal direction from a distal side of the needle seat.

In one embodiment, the button is formed by a side wall of the distal side portion of the handle; when the button is depressed, the button pushes the snapping part of the elastic arm away from the edge of the snap sleeve.

In one embodiment, the distal side portion of the hollow handle and the needle seat are made of a transparent material.

According to another aspect of the present disclosure, there is provided a retaining needle, the retaining needle comprising:

a hollow handle;
a needle seat at least partially disposed within the handle;
a puncture needle fixed to a distal end of the needle seat;
a catheter disposed outside of the puncture needle and a catheter hub; a safety mechanism, the safety mechanism comprising: a snapping step disposed on the handle; at least one elastic arm radially spreading outward disposed on the needle seat, an end portion of the elastic arm has a snapping portion radially protruding outward, the snapping portion being engaged with the snapping step; a button disposed on a distal side portion of the handle, the button, when being depressed, pushing the elastic arm along a radial inward direction, such that while the snapping portion of the elastic arm is disengaged from the snapping step, the puncture needle stretching outside of the handle are retracted into the hollow handle by virtue of vacuum absorption within the hollow handle.

In one embodiment, a vacuum sealing plug is provided between a base seat of the needle seat and a lumen of the hollow handle, so as to form a vacuum within the handle.

In one embodiment, a vacuum sealing plug is provided between a base seat of the needle seat and a lumen of the snap sleeve of the hollow handle, so as to form a vacuum in the snap sleeve of the handle.

The safety mechanism for a retaining needle according to the present disclosure is ingenious and highly safe. The retaining needle with the safety mechanism according to the present disclosure not only has a high safety, but also operates simply and conveniently, thereby effectively preventing the retaining needle from hurting the user or any person in contact during use and thereafter.

BRIEF DESCRIPTION OF THE ACCOMPANYING DRAWINGS

Figure 1A:
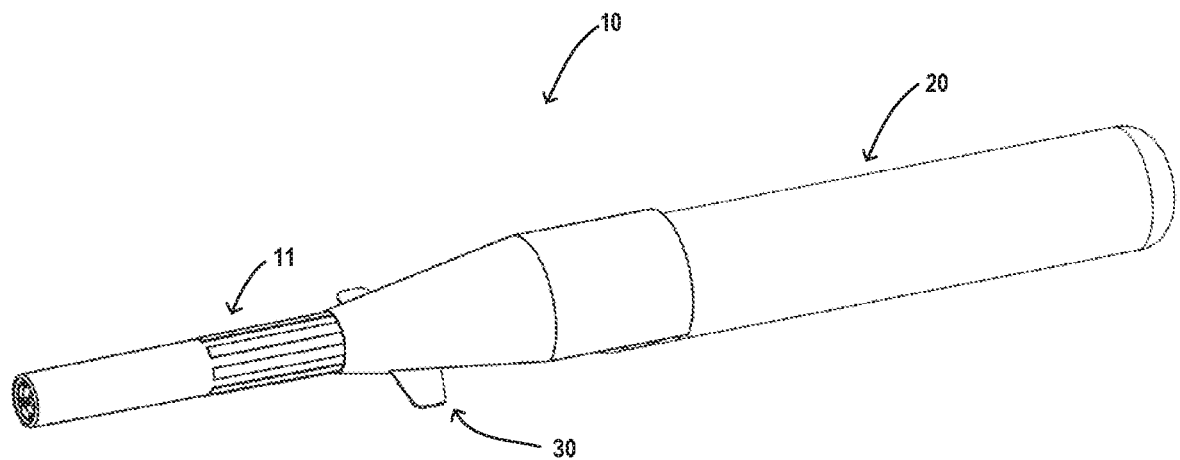
FIGS. 1A and 1B are stereoscopic diagrams of an unused retaining needle observed from different directions according to a first embodiment of the present utility mode.
Figure 1B:
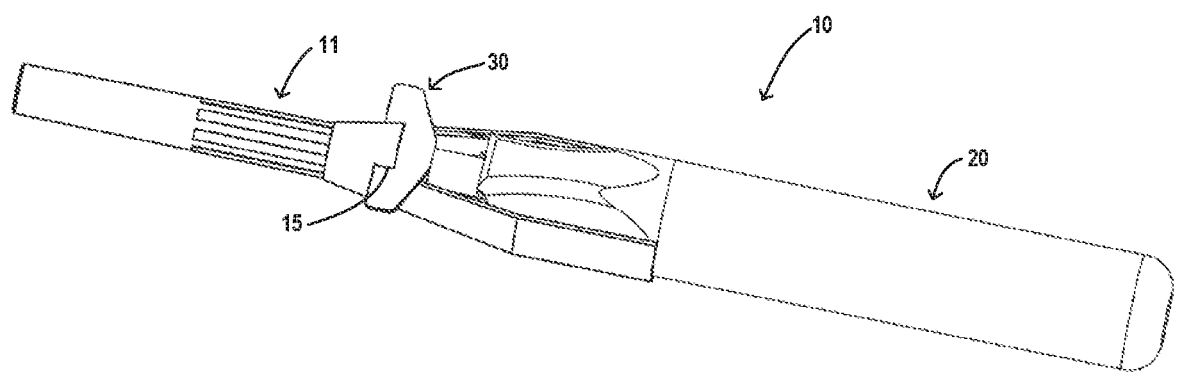
Figure 1C:
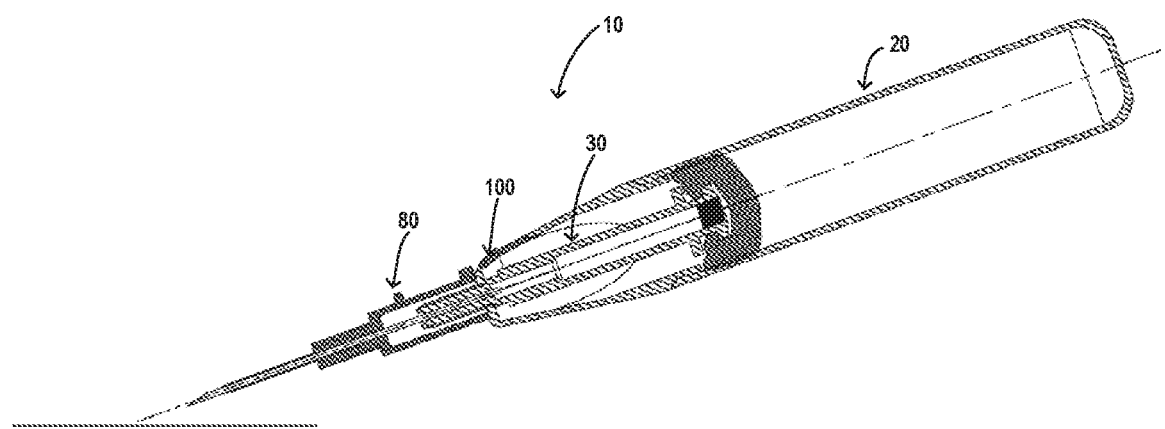
FIGS. 1C-1G illustrate a process of using a retaining needle according to the first embodiment of the present disclosure.
Figure 1D:
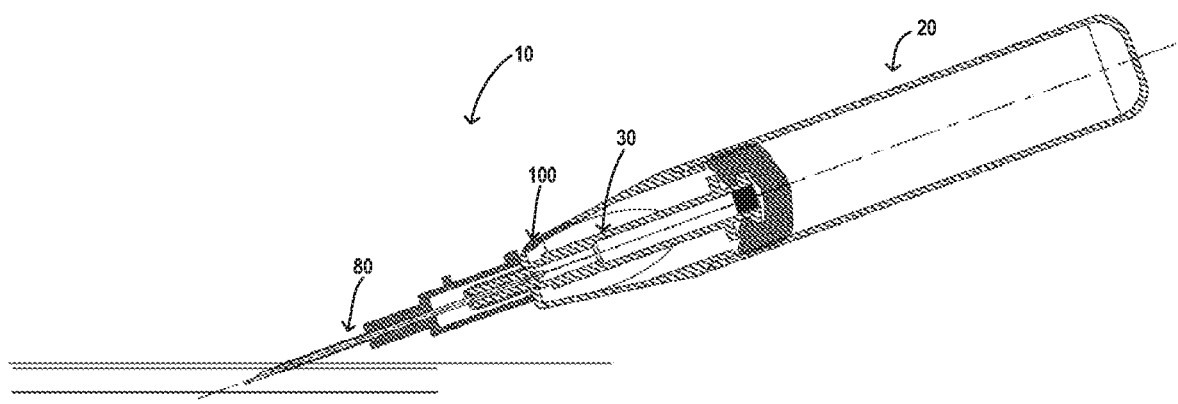
Figure 6A:
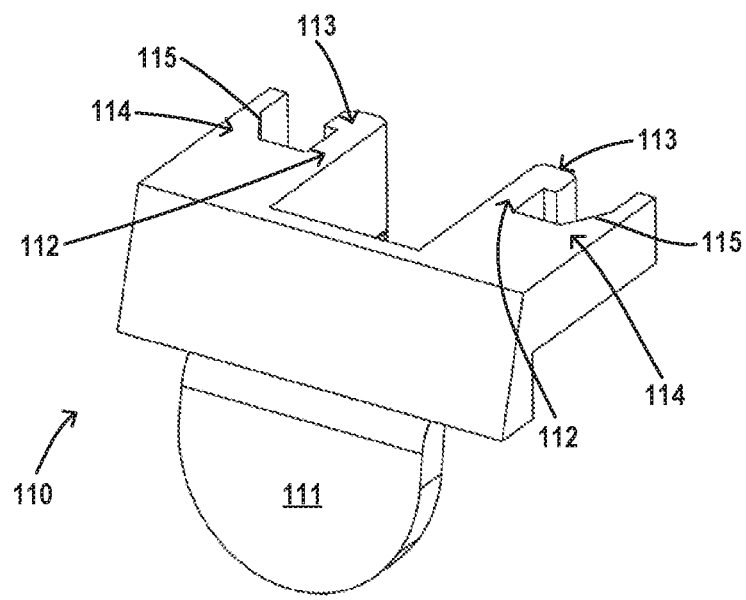
Figure 6B:
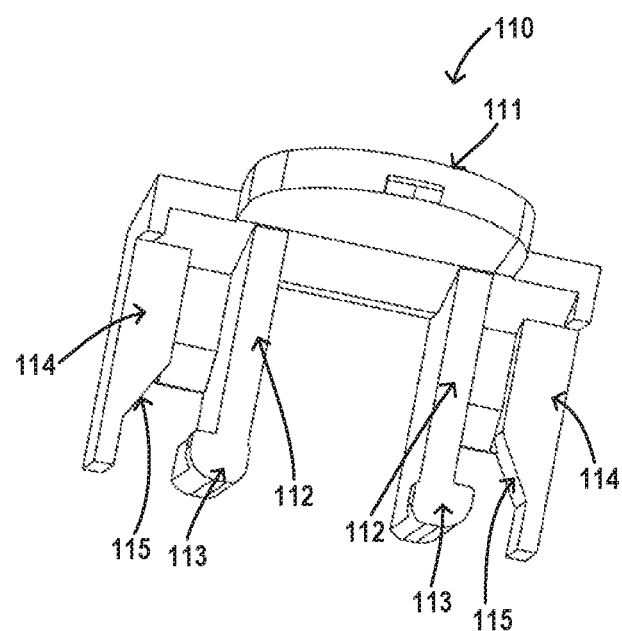
Figure 6C:
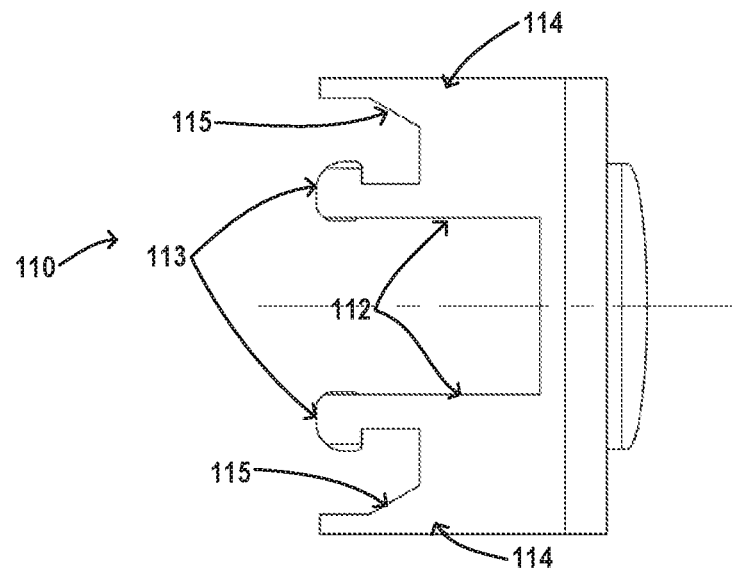

FIGS. 6A, 6B, and 6C are stereoscopic diagrams and top views of a button of the retaining needle according to the first embodiment illustrated in FIGS. 1A and 1B.

Figure 7:
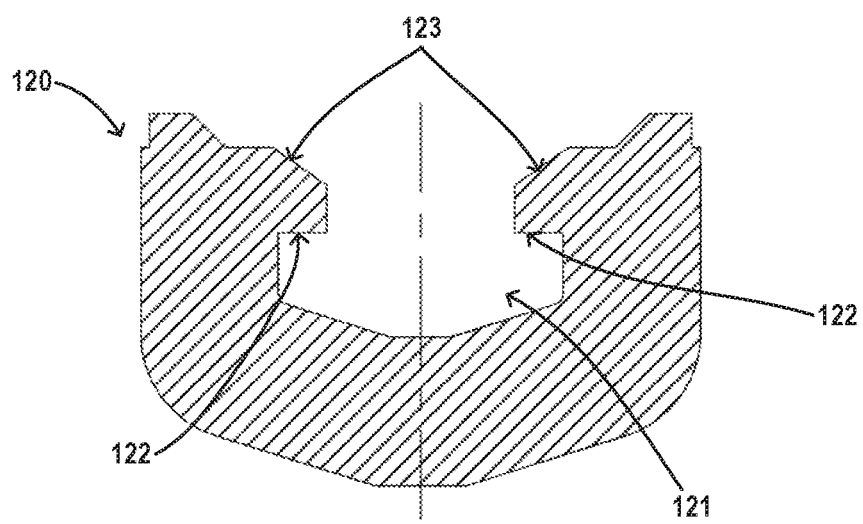

FIG. 7 illustrates a sectional view of a vacuum sealing plug of the retraining needle according to the first embodiment illustrated in FIGS. 1A and 1B.

FIGS. 8A, 8B, 8C, 8D, and 8E are stereoscopic diagrams and longitudinal sectional views of a catheter and catheter hub assembly of the retaining needle according to the first embodiment illustrated in FIGS. 1A and 1B observed from different directions.

Figure 9A:
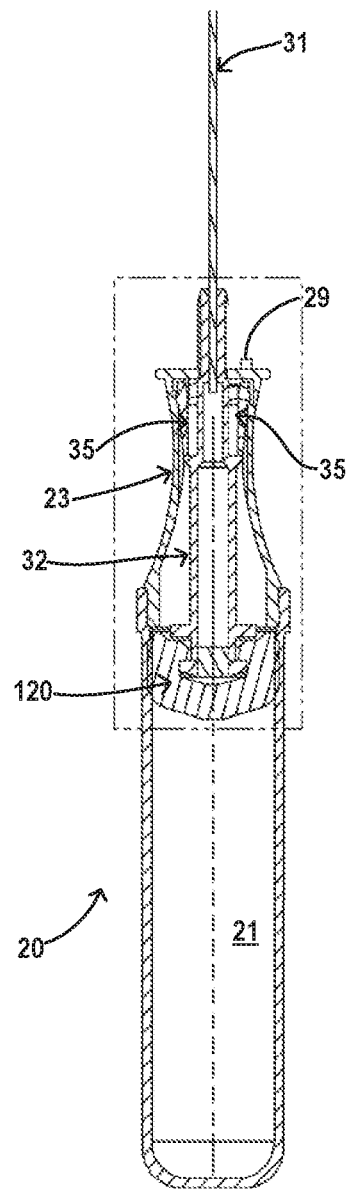
Figure 9B:
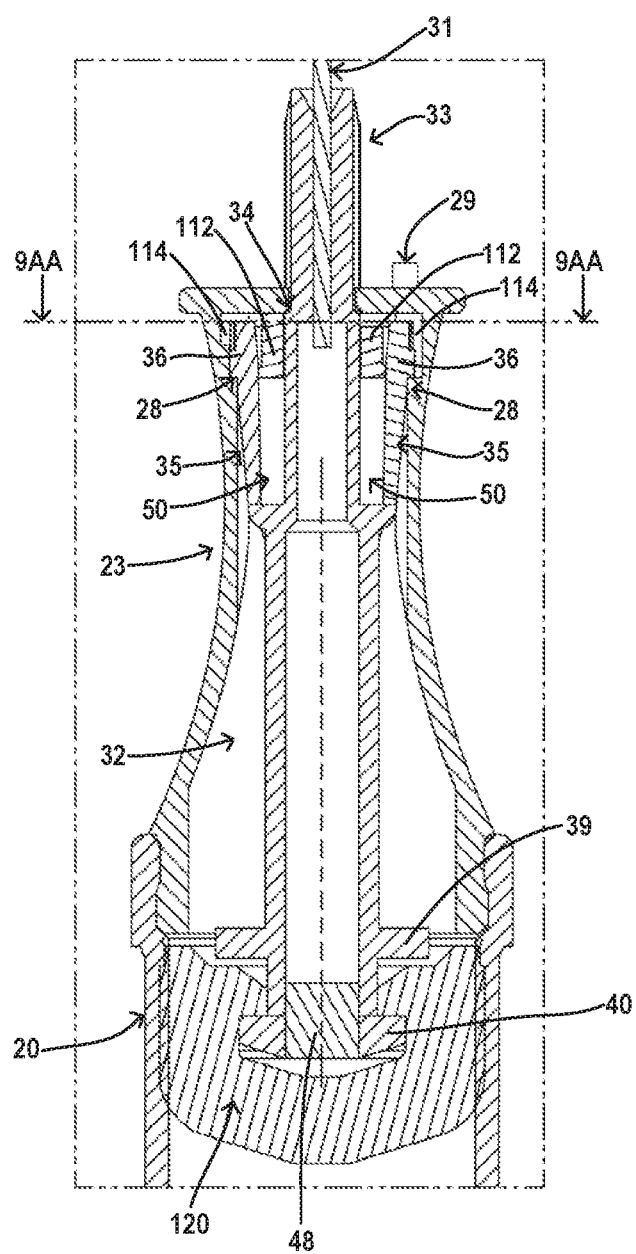
Figure 9C:
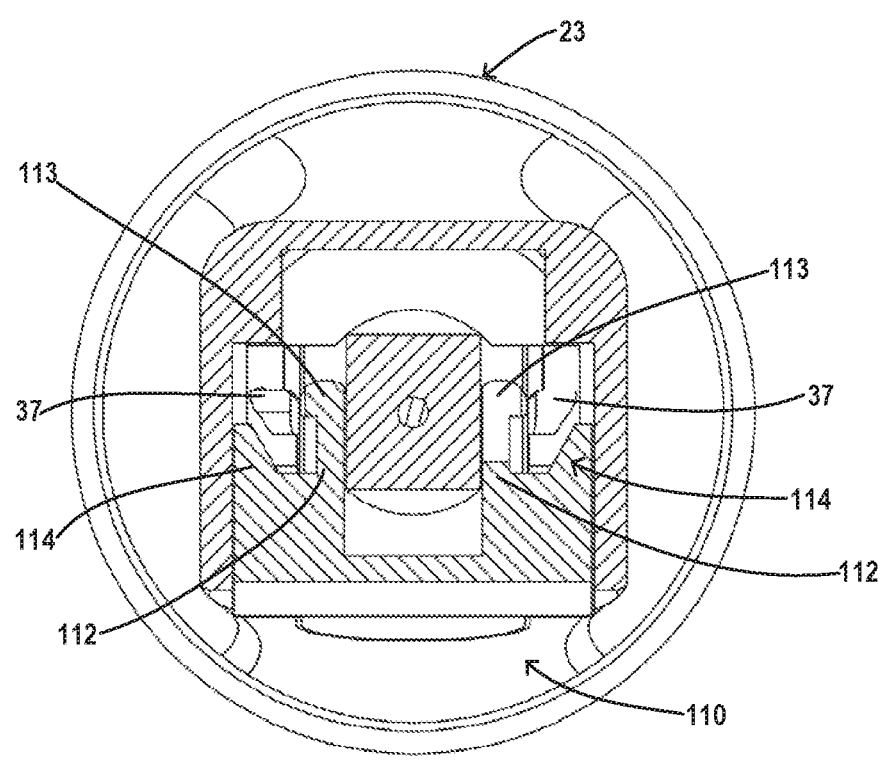

FIGS. 9A, 9B, and 9C are sectional views of different sections of a state when a button of a safety mechanism has not been depressed yet after the retaining needle according to the first embodiment as illustrated in FIGS. 1A and 1B is punctured into a blood vessel during use to push the catheter and the catheter hub assembly towards a distal side.

FIGS. 10A, 10B, 10C, 10D, 10E, 10F, 10G and 10H are section views of different directions of a state when the button of the safety mechanism is just depressed after the retaining needle according to the first embodiment as illustrated in FIGS. 1A and 1B is punctured into a blood vessel during use to push the catheter and the catheter hub assembly towards a distal side.

Figure 11A:
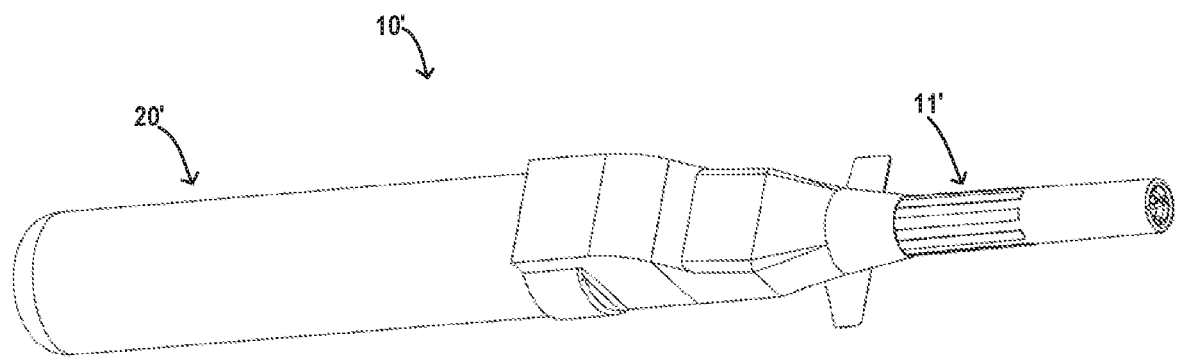
Figure 11B:
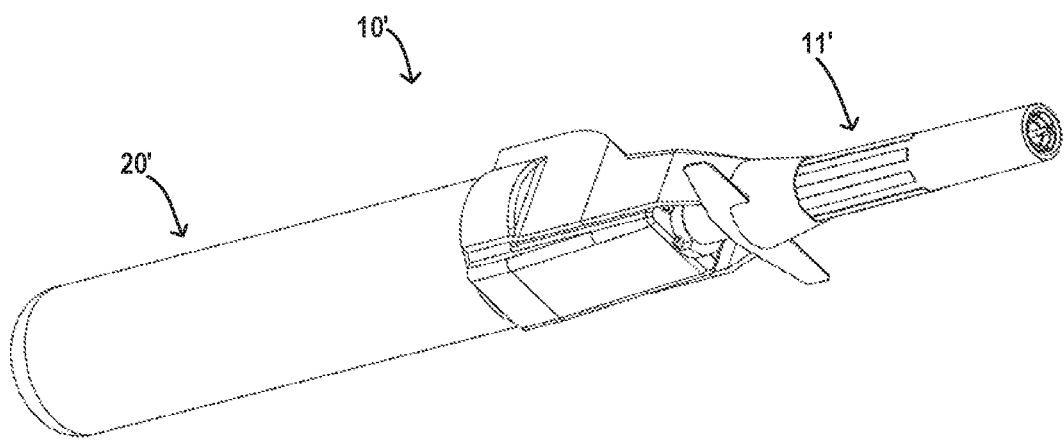

FIGS. 11A and 11B are stereoscopic diagrams of an unused retaining needed observed from different directions according to a second embodiment of the present disclosure.

Figures 12A, 12B:
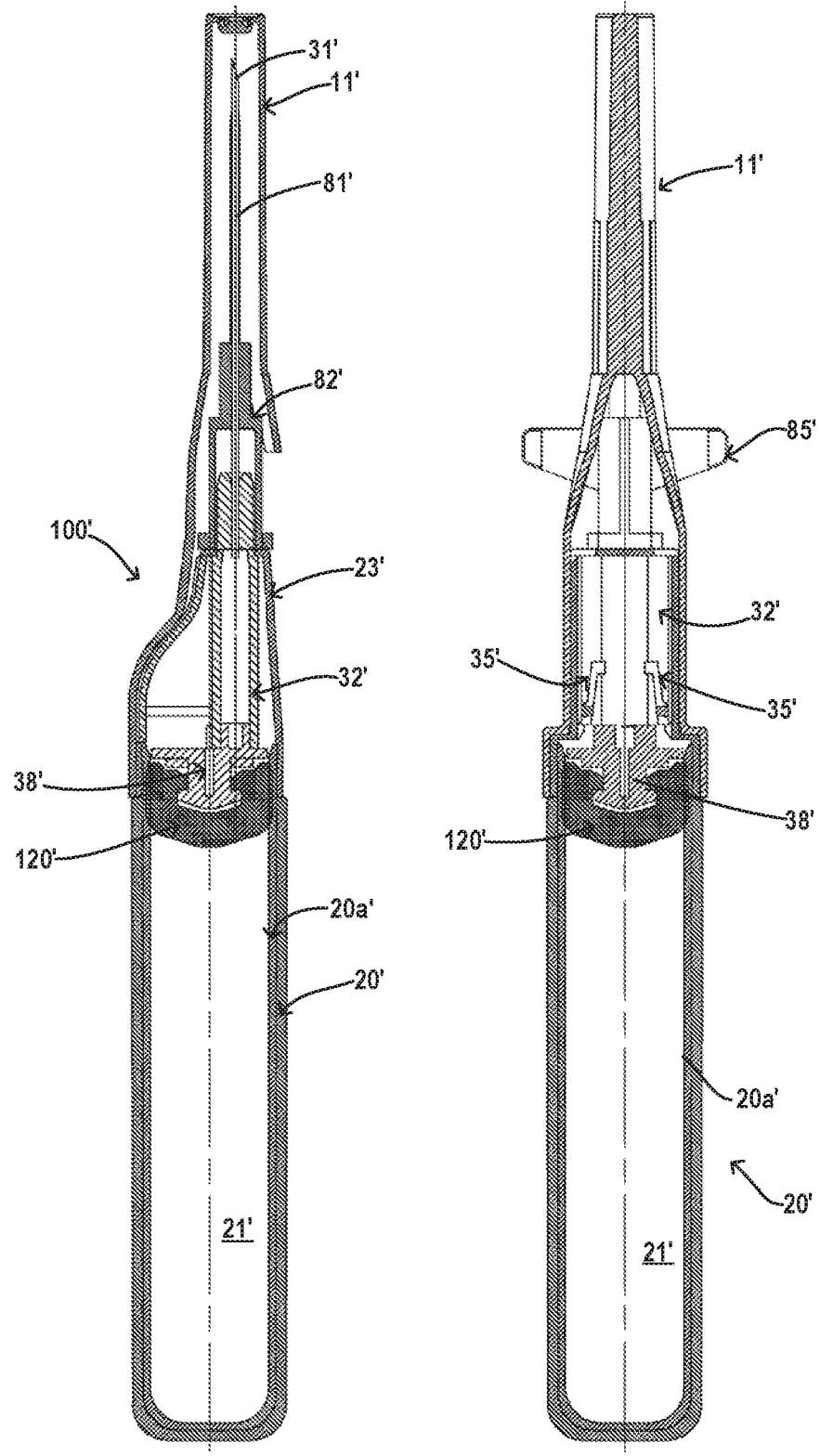

FIGS. 12A and 12B are longitudinal sectional views of the retaining needle according to the second embodiment as illustrated in FIGS. 11A and 11B sectioned from different sections.

Figure 13A:
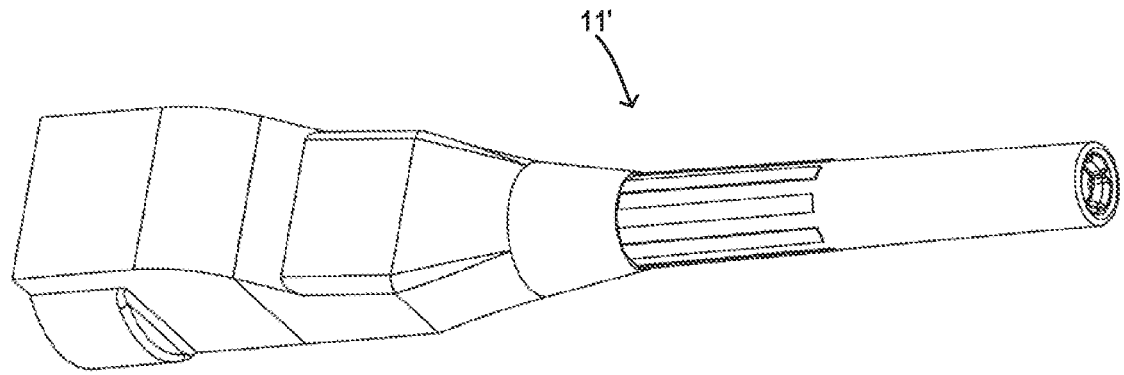
Figure 13B:
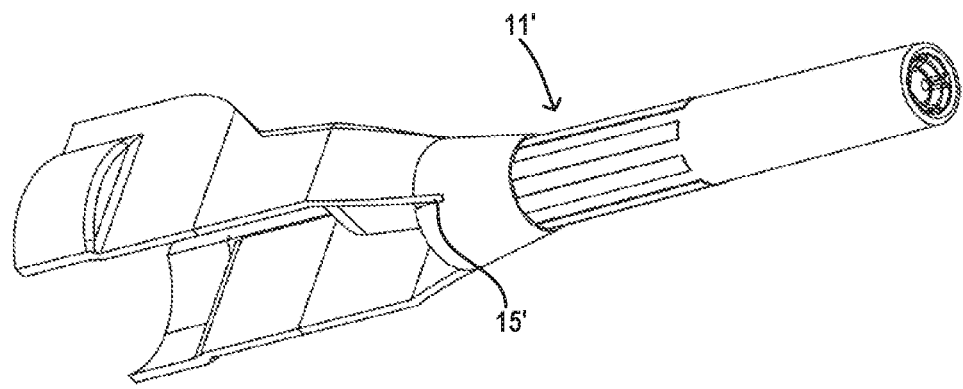
Figure 13C:
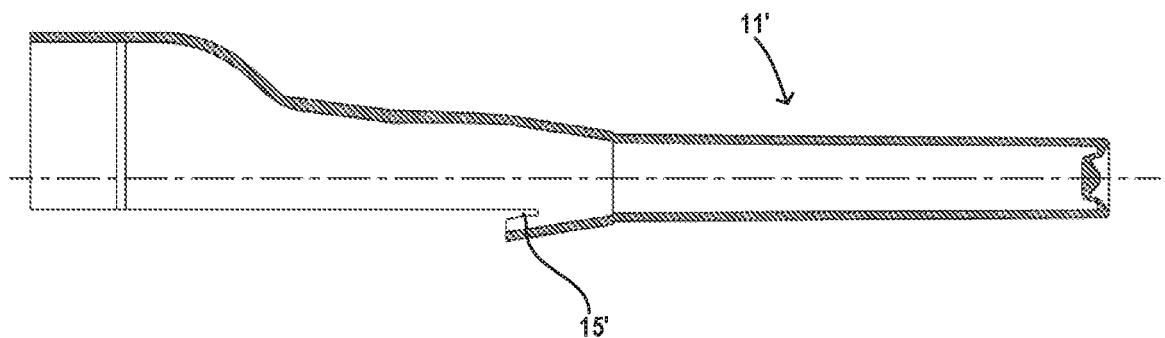

FIGS. 13A, 13B, and 13C are stereoscopic views and sectional views of a protection sheath of the retaining needle according to a second embodiment as illustrated in FIGS. 11A and 11B.

FIGS. 14A, 14B, 14C, and 14D are stereoscopic diagrams of a needle seat of the retaining needle according to the second embodiment as illustrated in FIGS. 11A and 11B and longitudinal sectional views sectioned from different sections.

FIGS. 15A, 15B, 15C, 15D, and 15E are stereoscopic diagrams of a base seat of the retaining needle according to the second embodiment as illustrated in FIGS. 11A and 11B and sectional views sectioned from different directions.

Figure 16A:
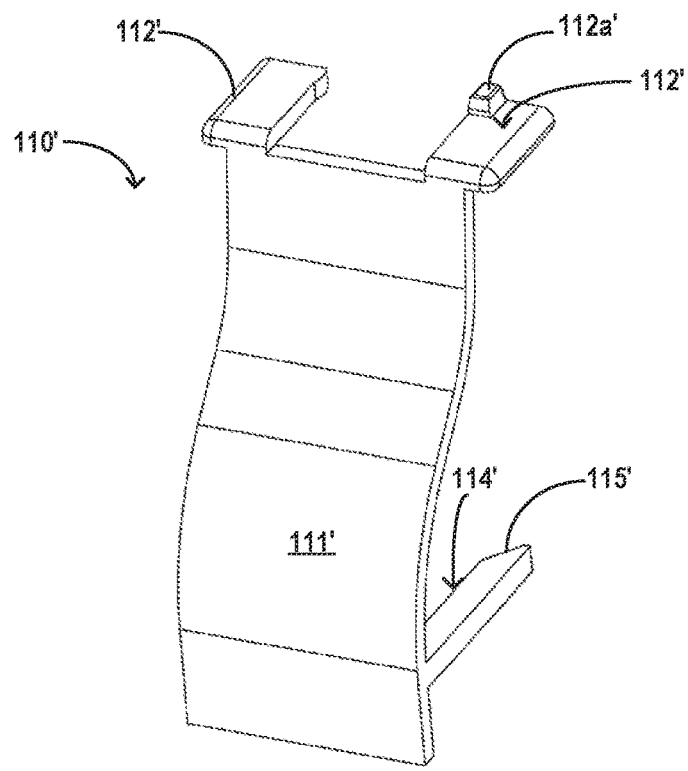
Figure 16B:
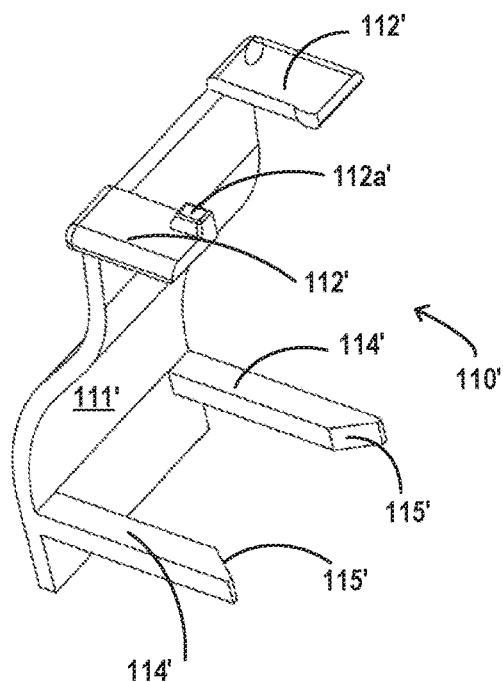

FIGS. 16A and 16B are stereoscopic diagrams of a button of a retaining needle according to the second embodiment as illustrated in FIGS. 11A and 11B.

Figure 17A:
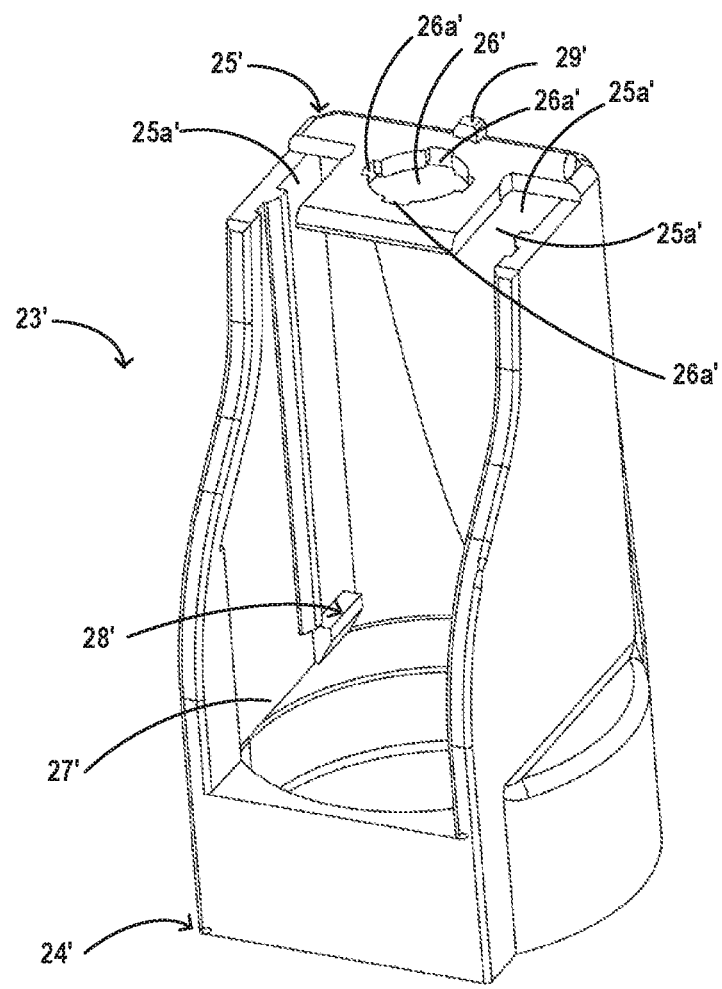
Figure 17B:
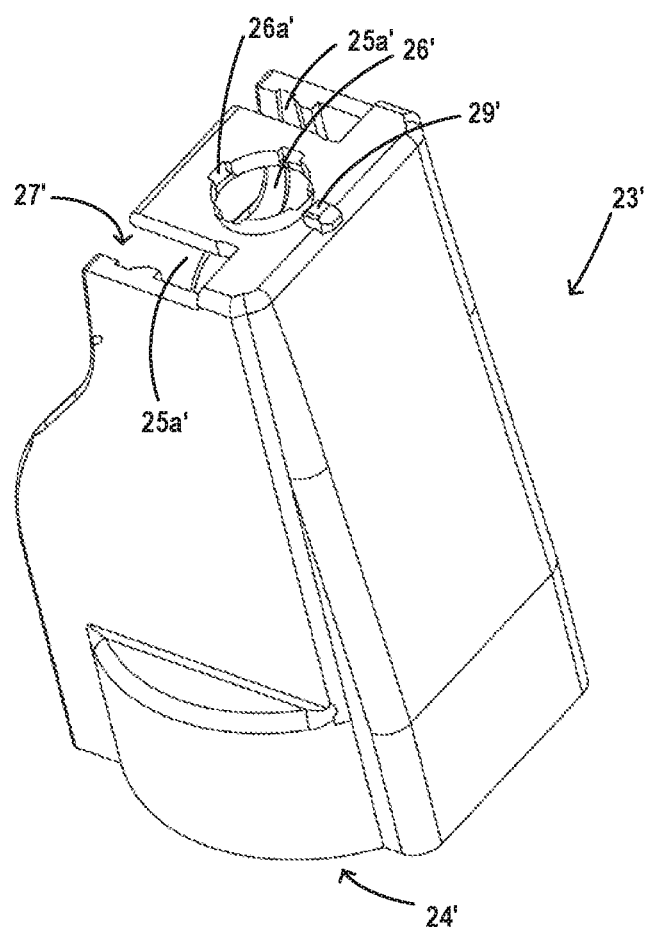

FIGS. 17A and 17B are stereoscopic diagrams of a handle distal side portion of a retaining needle according to the second embodiment as illustrated in FIGS. 11A and 11B.

Figure 18A:
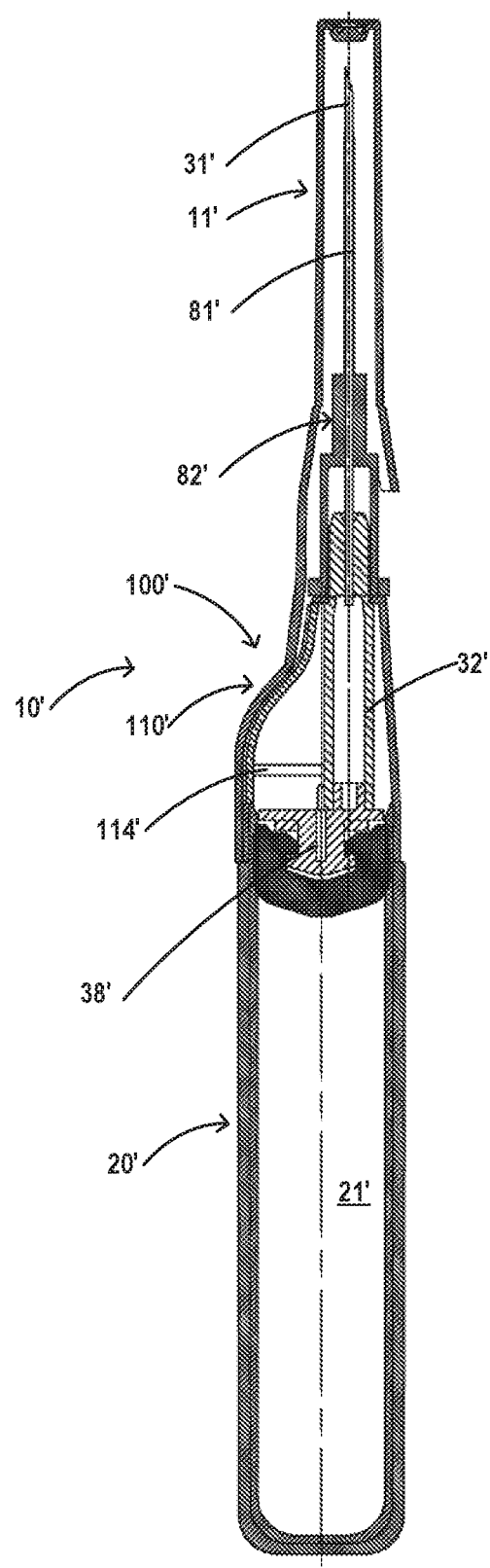
Figure 18B:
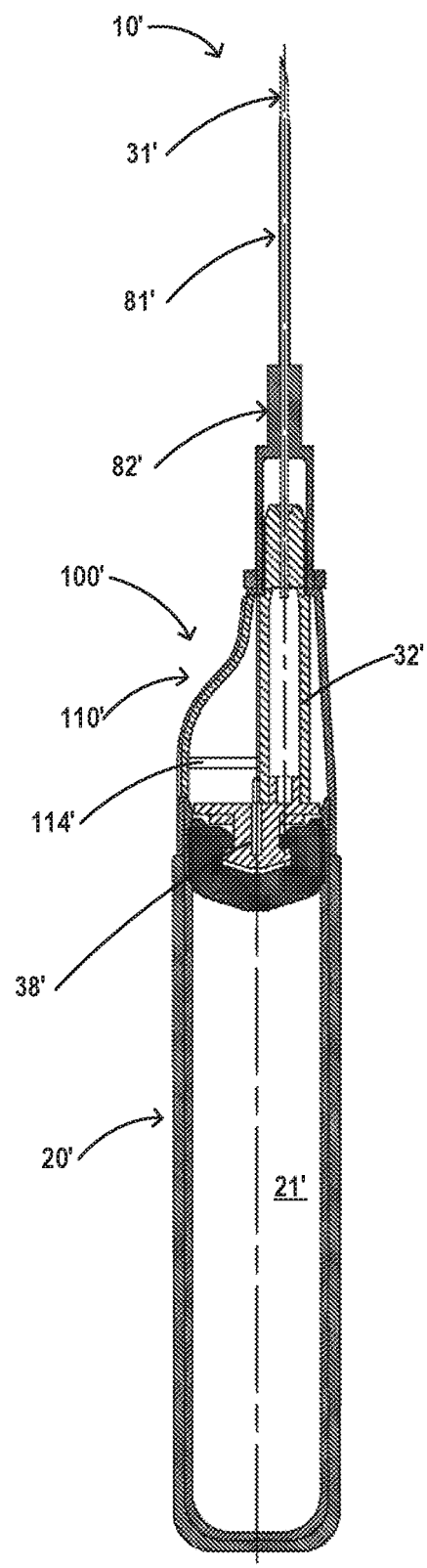
Figure 18C:
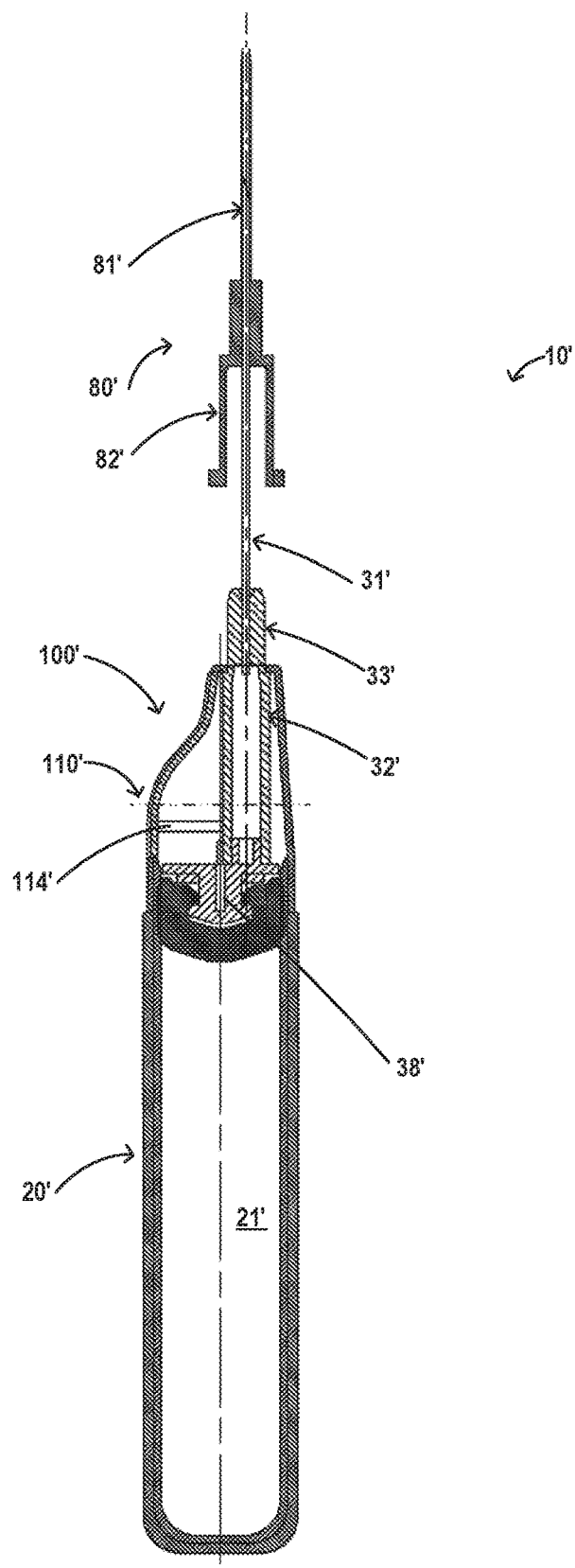
Figure 18D:
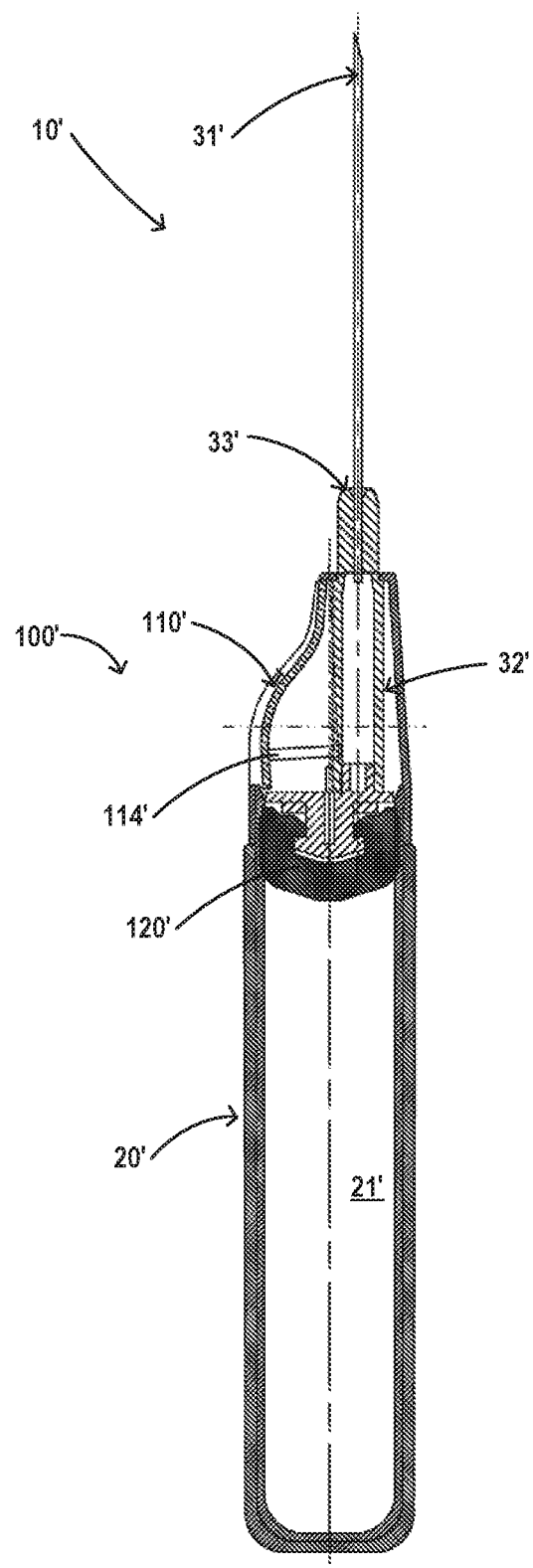
Figure 18E:
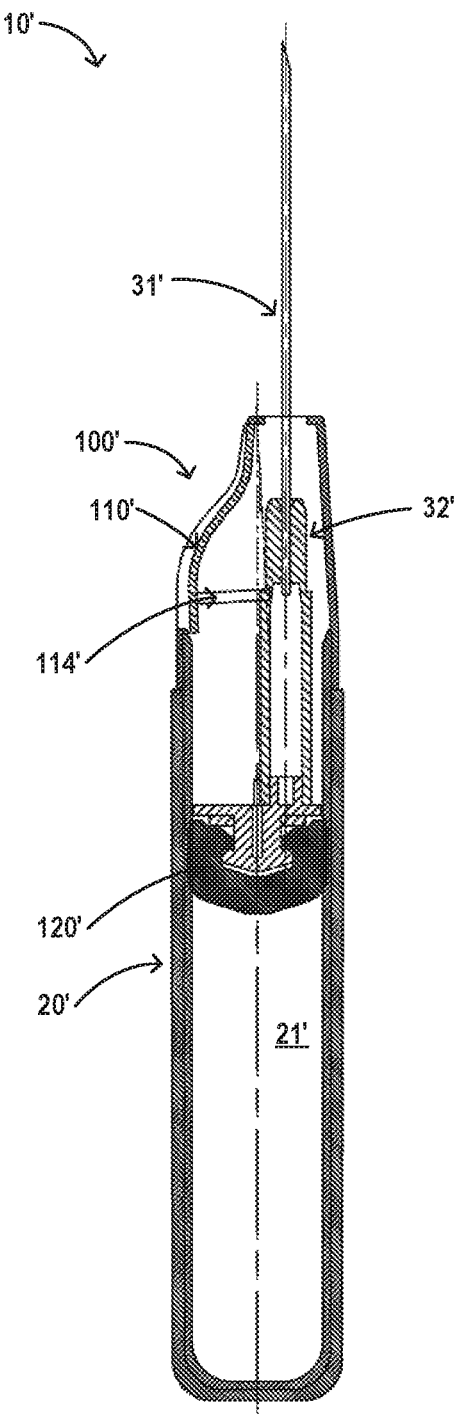
Figure 18F:
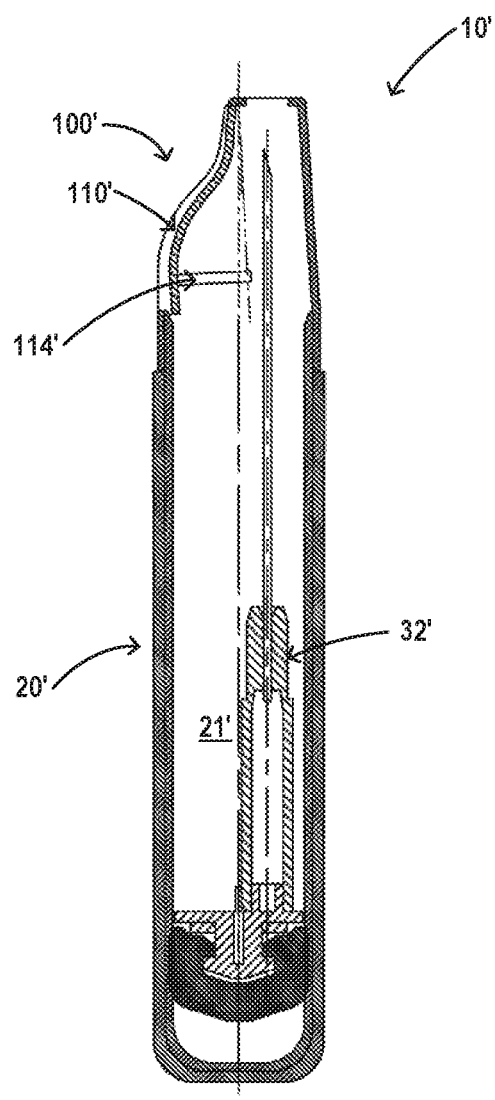

FIGS. 18A, 18B, 18C, 18D, 18E, and 18F are status diagrams of the retaining needle in use according to the second embodiment as illustrated in FIGS. 11A and 11B, wherein FIG. 18A illustrates a retaining needle without removal of the protection sheath, FIG. 18B illustrates a retaining needle with removal of the protection sheath; FIG. 18C illustrates a retaining needle that drives the catheter and the catheter hub assembly to the distal side; FIG. 18D illustrates a retaining needle with the button of the safety mechanism being depressed; FIGS. 18E and 18F illustrate a retaining needle with the puncture needle in a being retracted state and in an already retracted state.

Figure 19A:
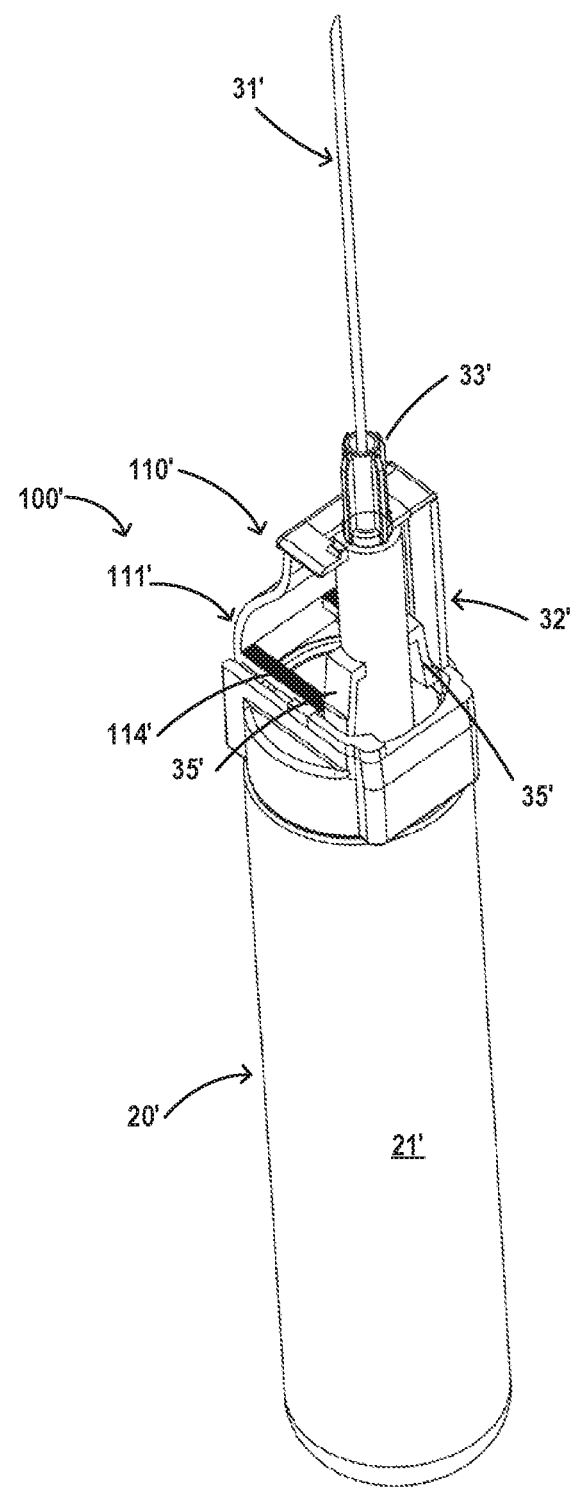
Figure 19B:
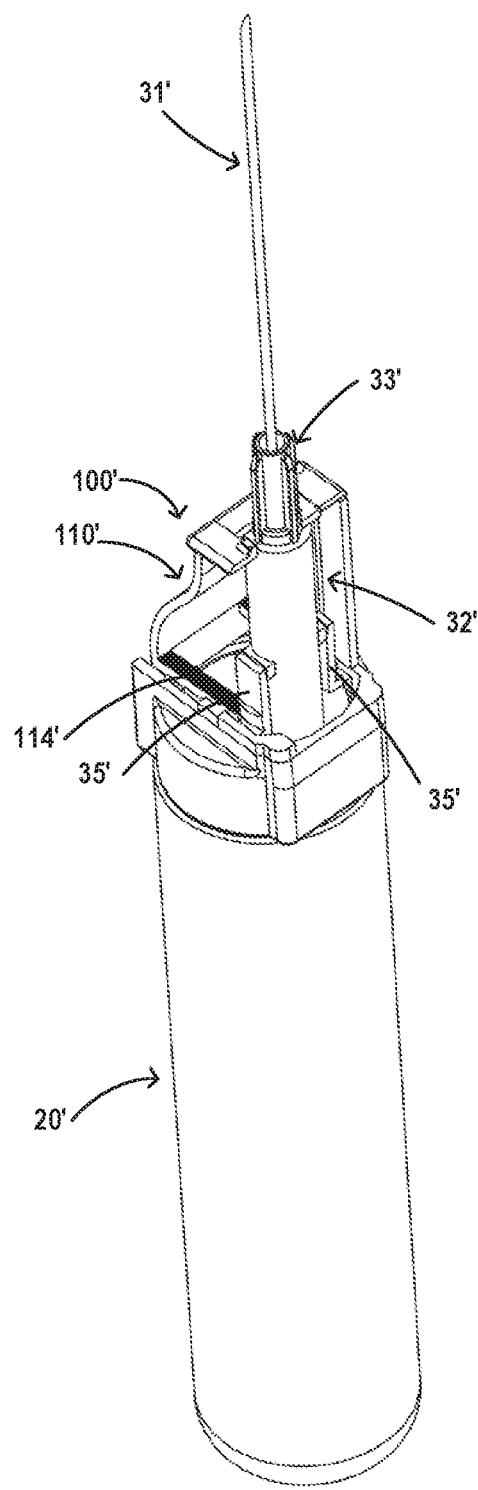

FIGS. 19A and 19B are views of mutual interaction between a driving arm of the button and the elastic arm of the needle seat when the button of the retaining needle is depressed according to the second embodiment as illustrated in FIGS. 11A and 11B.

Figure 20:
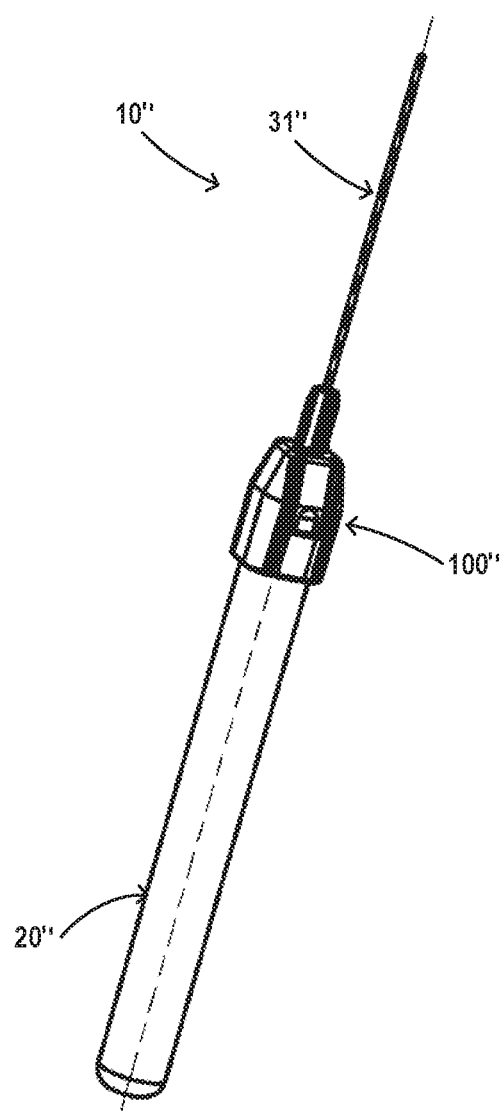

FIG. 20 illustrates a stereoscopic diagram of an unused retaining needle with removal of the protective sheath according to a third embodiment of the present disclosure.

Figure 21A:
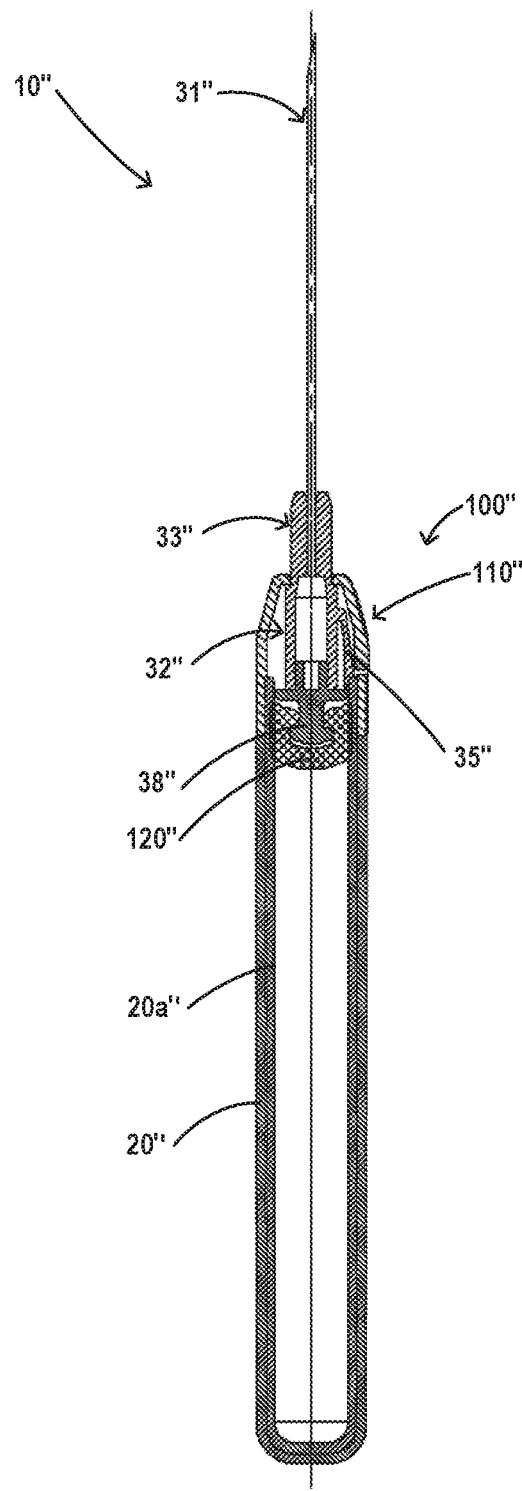
Figure 21B:
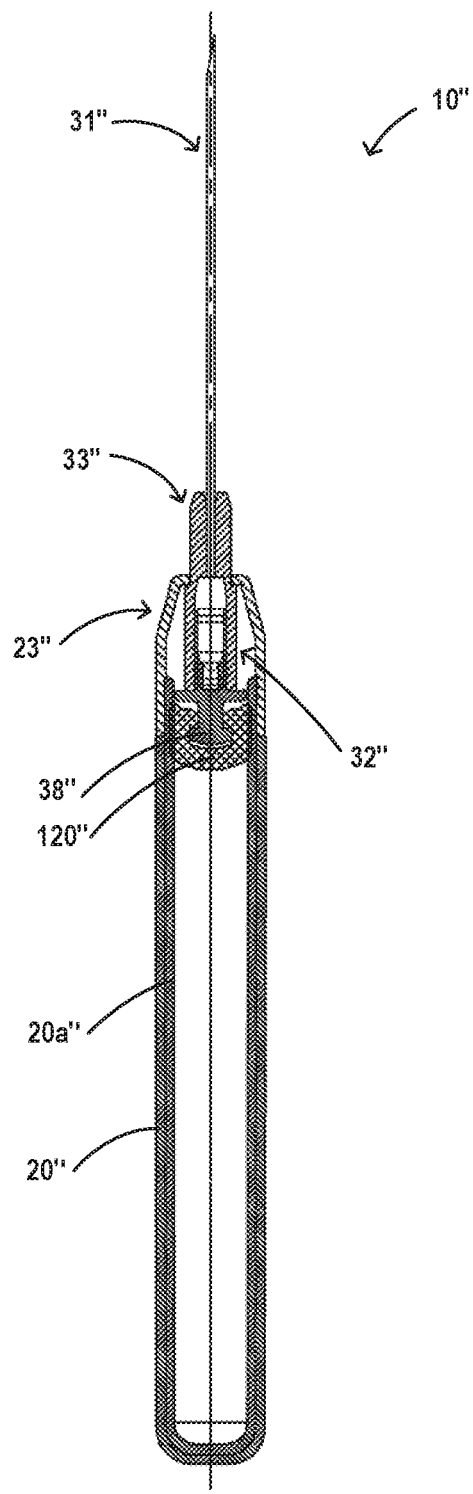

FIGS. 21A and 21B are longitudinal sectional views of an unused retaining needle sectioned from different sections according to a third embodiment of the present disclosure.

Figure 22A:
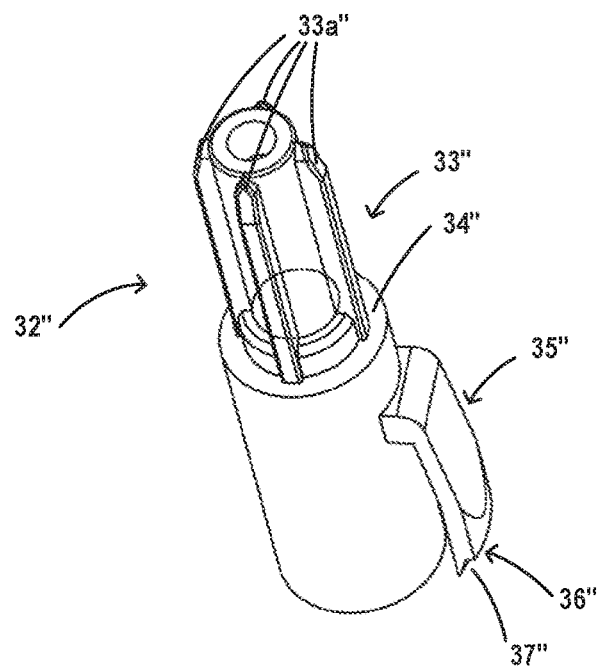
Figures 22B, 22C:
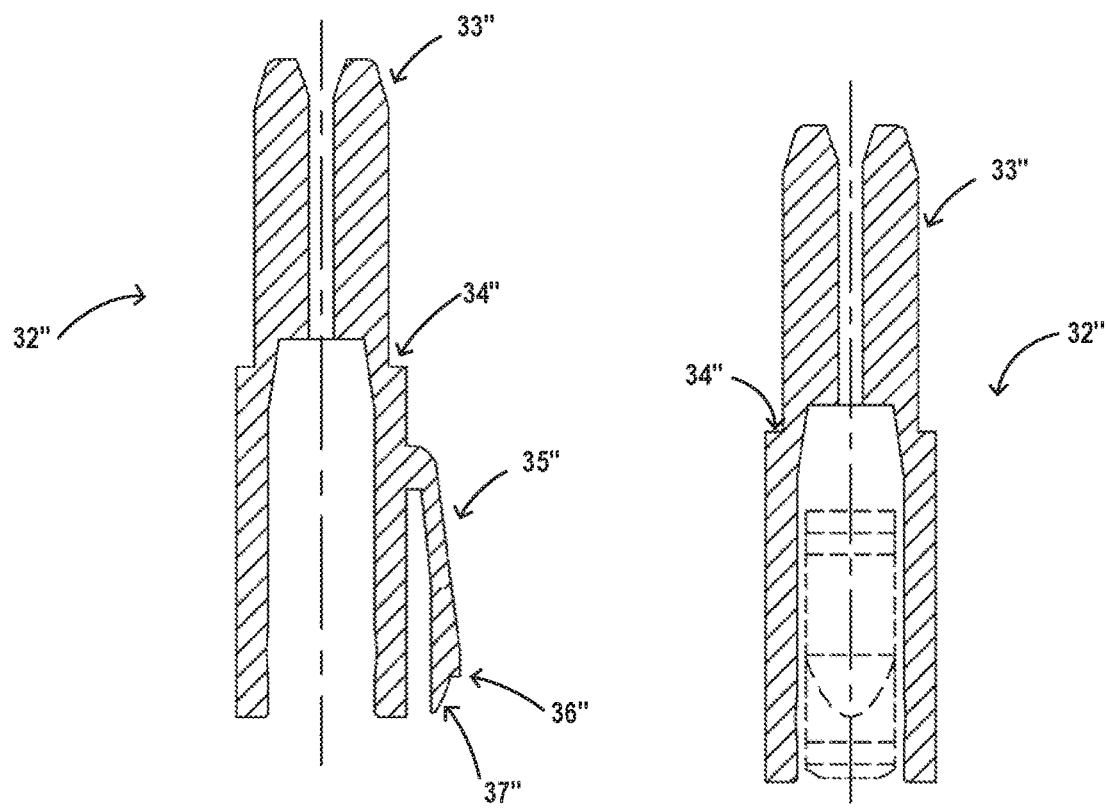

FIGS. 22A, 22B, and 22C are stereoscopic diagrams of a needle seat of a retaining needle according to the third embodiment as illustrated in FIG. 20 and longitudinal sectional views sectioned from different sides.

Figure 23A:
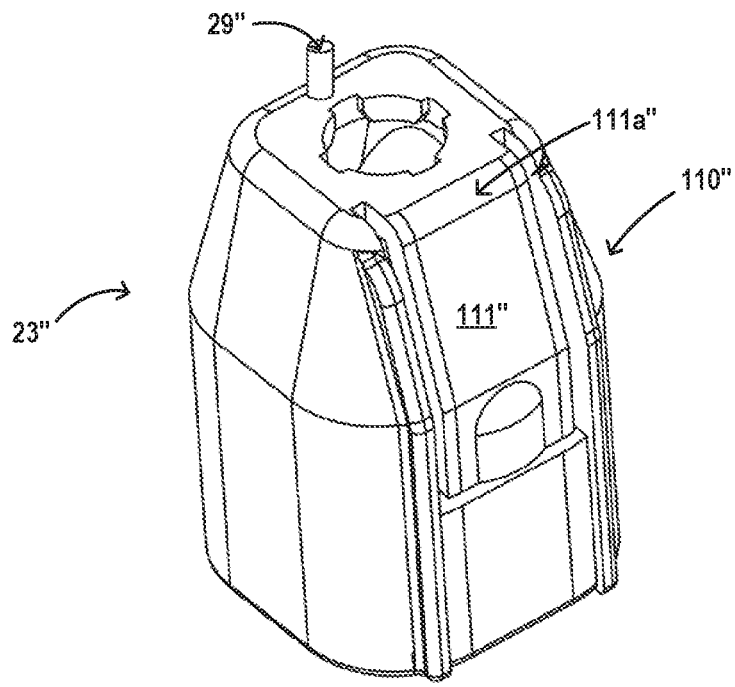
Figure 23B:
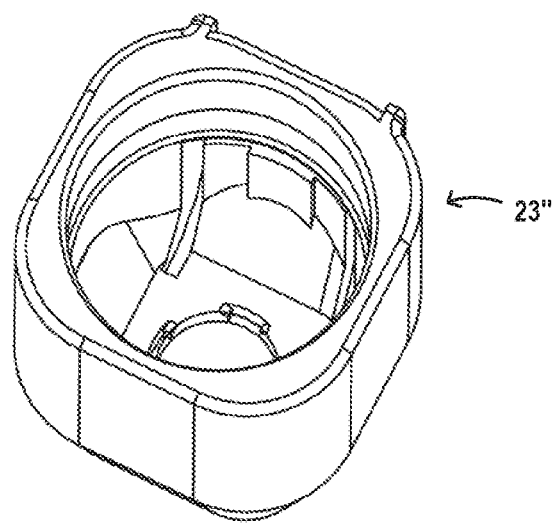

FIGS. 23A and 23B are stereoscopic diagrams of a handle distal side portion of a retaining needle according to the third embodiment as illustrated in FIG. 20.

Figure 24:
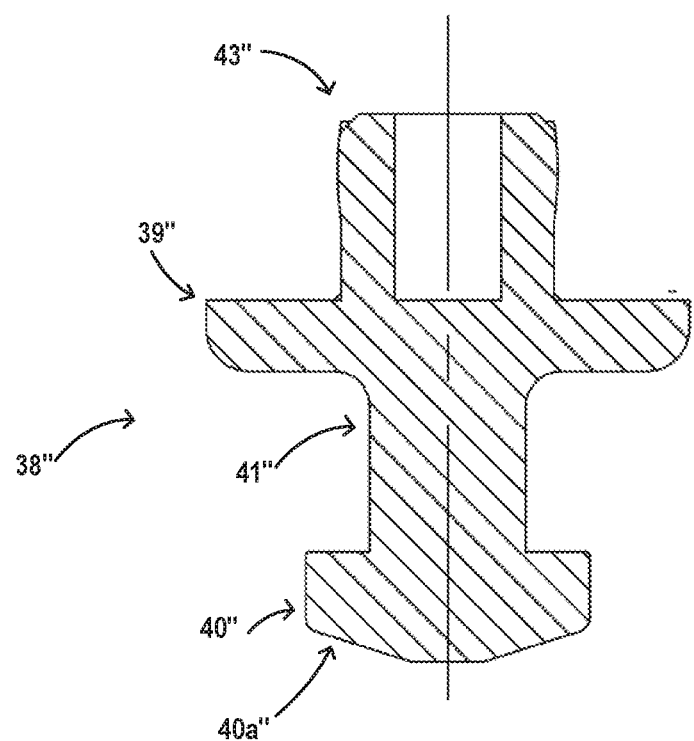

FIG. 24 illustrates a sectional view of a needle seat base seat of the retaining needle according to the third embodiment as illustrated in FIG. 20.

Figure 25:
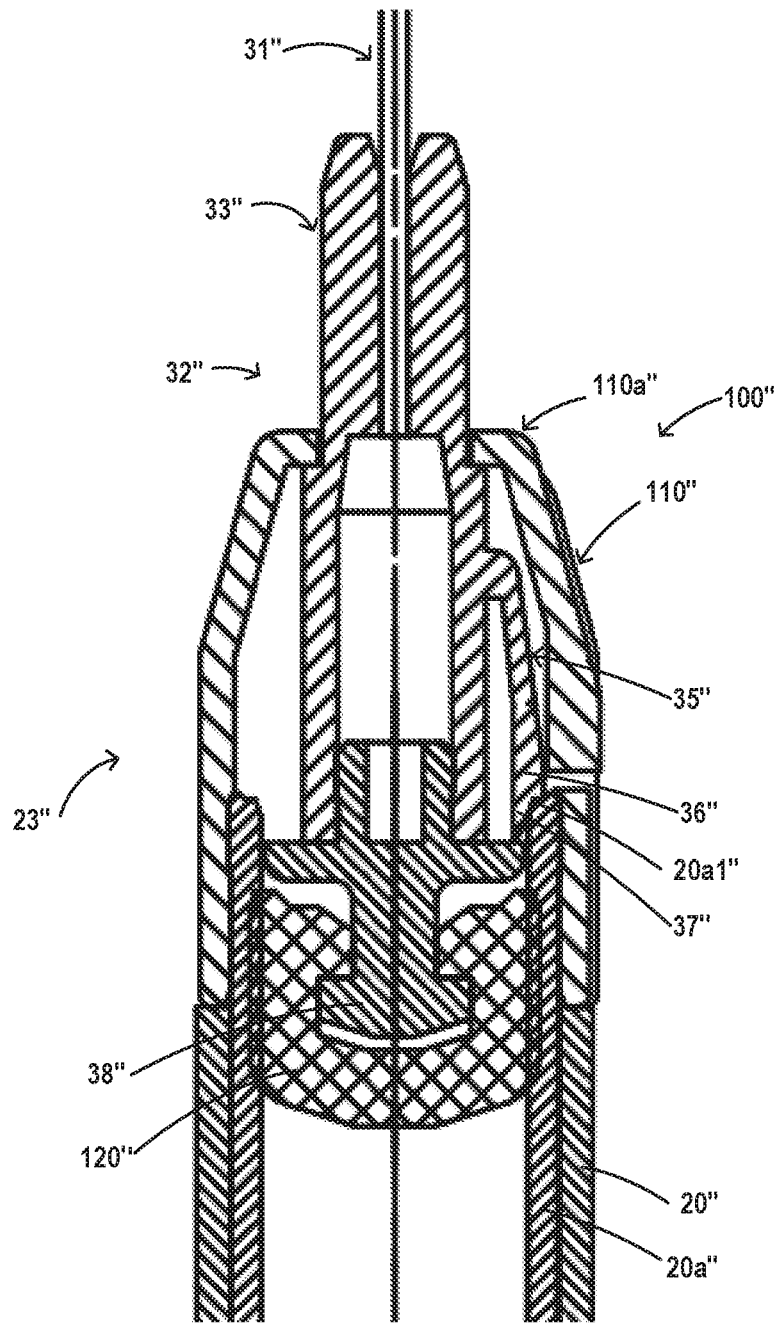

FIG. 25 is a partially enlarged view of FIG. 21A, which illustrates a cooperation relationship among the button, the elastic arm of the needle seat and the snap sleeve when the safety mechanism is not launched.

Figure 26:
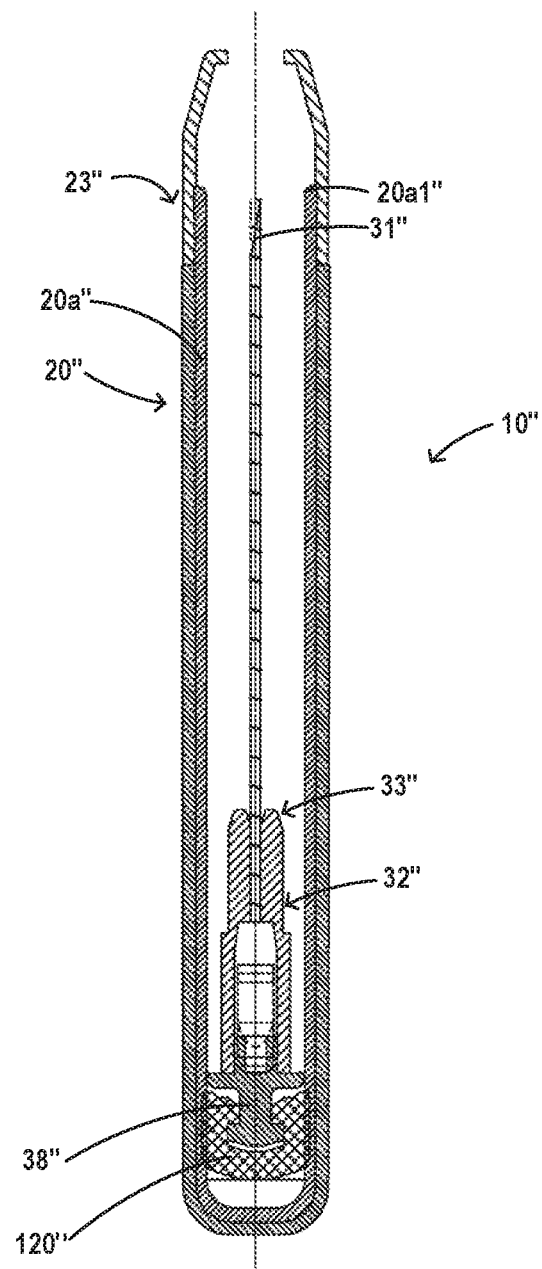

FIG. 26 is a sectional view of the puncture needle of the retaining needle according to the third embodiment as illustrated in FIG. 20 which is retracted within the handle after the button is depressed.

Figure 27A:
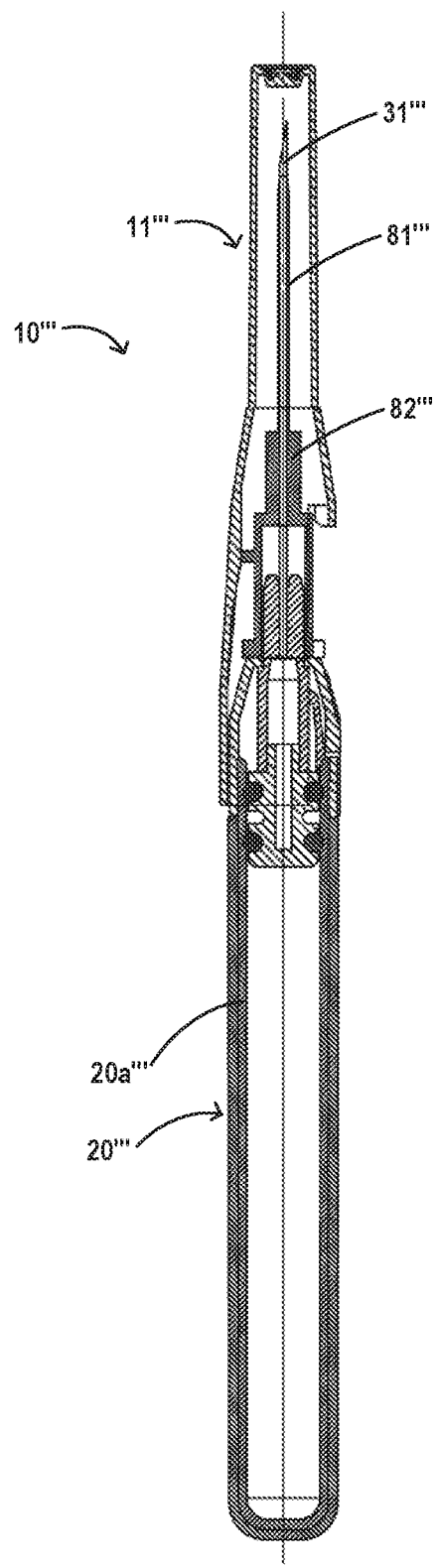
Figure 27B:
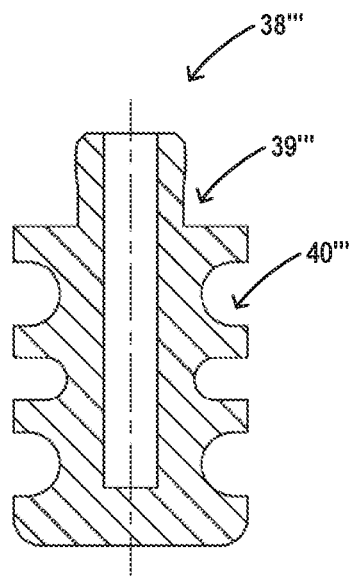
Figure 27C:
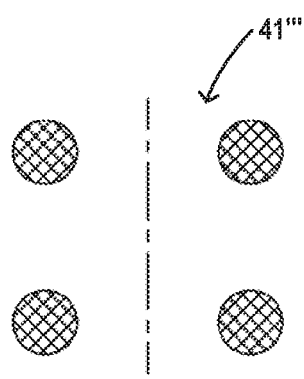

FIGS. 27A, 27B, and 27C illustrate a fourth embodiment of the present disclosure, which are a sectional view of the retaining needle of the fourth embodiment, a longitudinal sectional view of a needle seat base seat, and a longitudinal sectional view of the O-shaped sealing ring, respectively.

DETAILED DESCRIPTION OF THE PREFERRED EMBODIMENTS

According to a design idea of the present disclosure, a plurality of preferred embodiments exist to implement objectives of the present disclosure. Hereinafter, a structure, configuration and working principle of the retaining needle of the present disclosure will be interpreted with reference to the preferred embodiments as illustrated in the drawings. Those skilled in the art may envisage other embodiments of implementing the objectives of the present disclosure with reference to the illustrated preferred embodiments.

In the present specification, the term "proximal side" refers to a side of a medical instrument closer to an operation, while the term "distal side" refers to a side of the medical instrument distant from the operator; terms "upper," "lower," "left" and "right" are indicated relative to the figure surface; terms "longitudinal" and "radial" are indicated relative to the longitudinal axis of the instrument. Besides, same components are represented by same reference numerals.

Figure 2A:
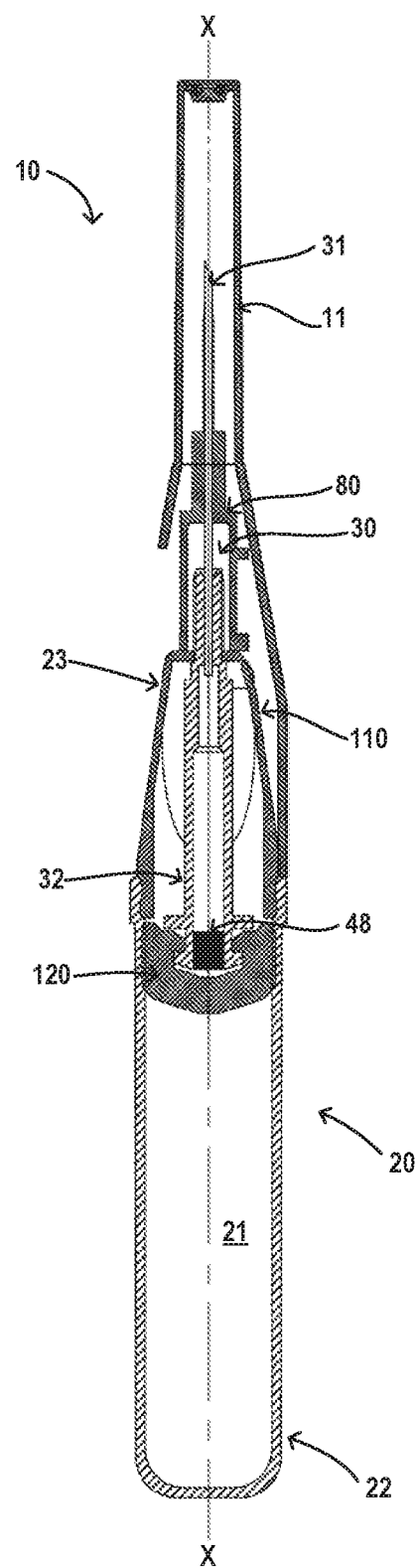
FIGS. 2A and 2B are longitudinal sectional views of the retaining needle along different sections according to the first embodiment as illustrated in FIGS. 1A and 1B.
Figure 2B:
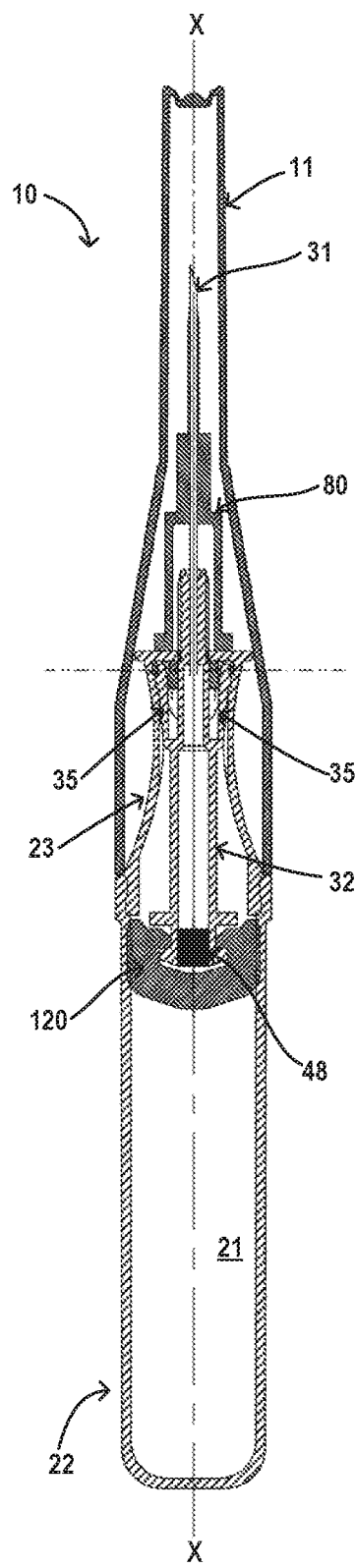

FIGS. 1A and 1B are stereoscopic diagrams of an unused retaining needle 10 observed from obliquely above and from obliquely down according to a first preferred embodiment of the present disclosure. FIGS. 2A and 2B are longitudinally sectional views of the retaining needle 10 according to the first embodiment as illustrated in FIGS. 1A and 1B along different sections. The retaining needle 10 has a longitudinal axis X-X (as illustrated in FIGS. 2A and 2B). The retaining needle 10 comprises: a hollow handle 20; a needle and needle seat assembly 30 at least partially disposed within the handle 20; a catheter and catheter hub assembly 80 disposed at a distal side of the handle 20 and surrounding a part of the needle and the needle seat assembly 30; and a security mechanism 100. Preferably, the retaining needle 10 further comprises a protection sheath 11 disposed at a distal end of the retaining needle for preventing the unused retaining needle from puncturing a person in contact.

Figure 1E:
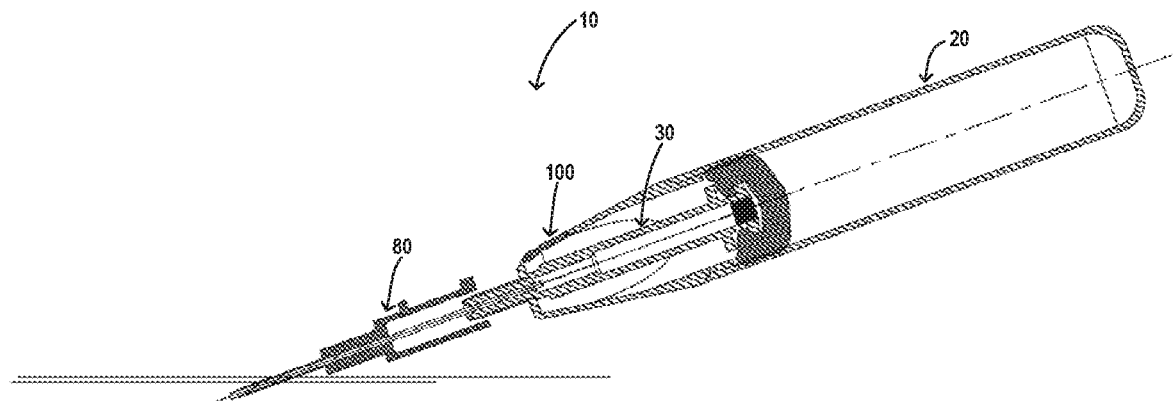
Figure 1F:
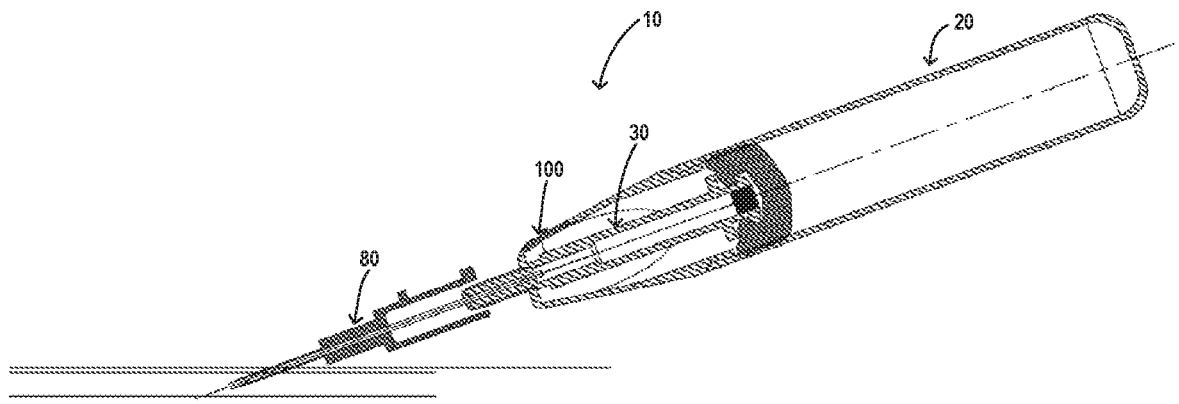
Figure 1G:
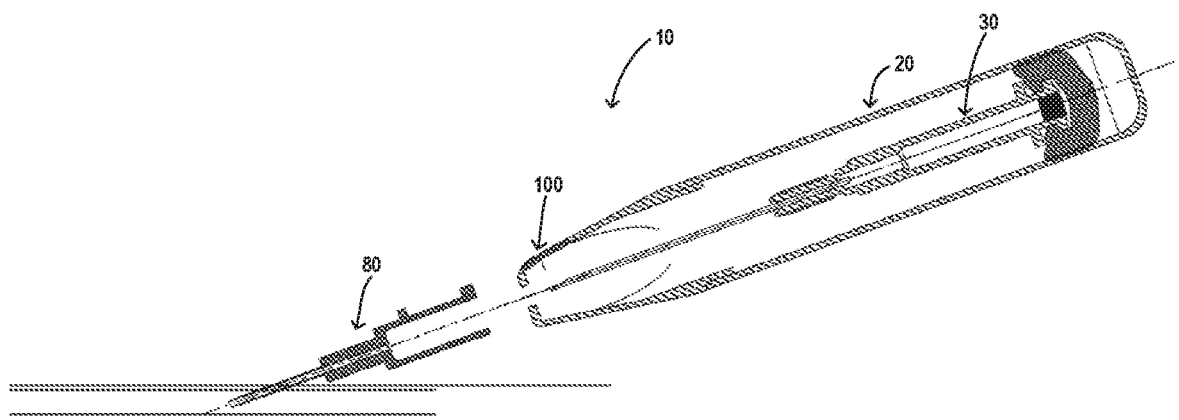

FIGS. 1C-1G illustrate a use process of the retaining needle 10 of the present disclosure. In preparation for use, the protection sheath 11 is first removed from the retaining needle 10, and the puncture needle of the retaining needle 10 is pieced into the blood vessel (see FIGS. 1C and 1D). After observing that the blood enters into the puncture needle and/or needle seat, the catheter and catheter hub assembly 80 is advanced to the distal side (as shown in FIG. 1E). After the catheter is in place, one hand presses a wing sheet of the catheter and catheter hub assembly 80, while the other hand presses the safety mechanism 100 (see FIG. 1F). The button of the safety mechanism 100 causes the needle and needle seat assembly 30 to be disengaged from the catheter and catheter hub assembly 80; the puncture needle, together with the needle seat, is retracted within a lumen of the handle 20 by virtue of vacuum in the hollow handle 20, thereby preventing the user from being punctured by the used puncture needle, which enhances security. Hereinafter, specific structures and engaging manners of respective components of the retaining needle 10 will be described in detail.

Figure 5A:
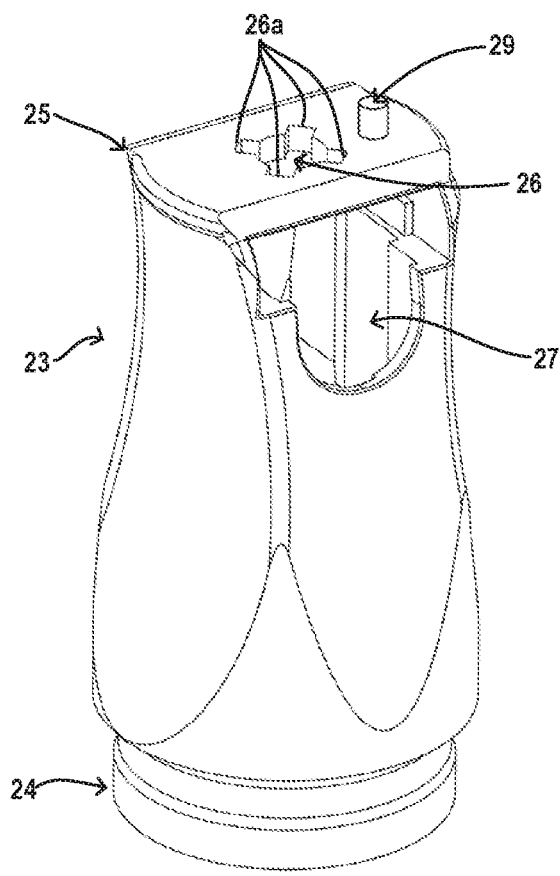
FIGS. 5A and 5B are stereoscopic diagrams of a handle distal side portion of the retaining needle illustrated in FIGS. 1A and 1B observed from different directions.
Figure 5B:
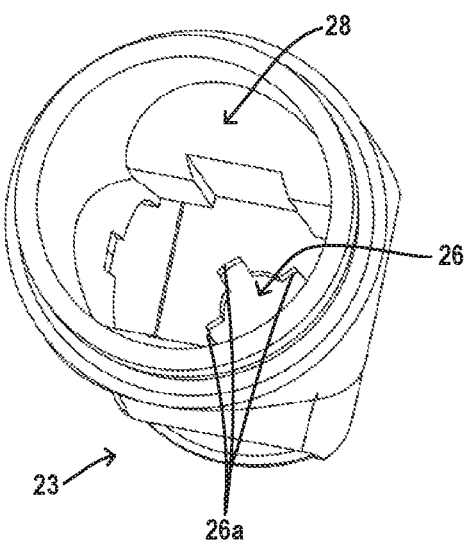

As illustrated in FIGS. 2A and 2B, the hollow handle 20 comprises a lumen 21, a proximal side portion 22, and a distal side portion 23. The proximal side portion 22 of the handle 20 is substantially cylindrical; the proximal end of the cylinder is closed, while the distal end is open, for engaging with the distal side portion 23 of the handle 20. FIGS. 5A and 5B are stereoscopic diagrams of the distal side portion 23 of the handle 20 of the retaining needle according to the first embodiment illustrated in FIGS. A1 and 1B observed from different directions, respectively. The distal side portion 23 of the handle 20 has an open proximal end 24 engaged with an open distal end of the proximal side portion 22. Besides, the distal end 25 of the distal side portion 23 is closed; the distal end 25 has a patterned hole 26. As illustrated in FIG. 5A, the so-called patterned hole means forming a plurality of notches 26a on a normal round hole. Of course, the shape of a patterned hole 26 is not limited to that, as long as it cooperates with a corresponding portion of the needle seat (which will be detailed hereinafter). Besides, a sidewall of the distal side portion 23 has a button hole 27 of the button 110 for receiving a safety mechanism 100. A snapping step 28 (see FIGS. 9B and 10C) that protrudes inwardly is provided on the inner wall of the distal side portion 23. The snapping step 28 is for engaging an elastic arm of the needle seat, which will be detailed later. Besides, in order to join the catheter and catheter hub assembly 80, a bulge 29 extending to the distal side is also formed on an end face (i.e., the end face formed with the patterned hole 26) of the distal end 25 of the distal side portion 23 of the handle 20 (see FIGS. 5A, 9A, 9B, 10B, and 10C).

Still referring to FIGS. 2A and 2B, the needle and needle seat assembly 30 comprises a puncture needle 31 and a needle seat 32. The puncture needle 31 is hollow and has a sharp distal end for puncturing a patient's skin. A proximal end of the puncture needle 31 is fixed to a distal end of the needle seat 32. FIGS. 4A, 4B, 4C, and 4D are stereoscopic diagrams of the needle seat of the retaining needle of the first embodiment as illustrated in FIGS. 1A and 1B and longitudinal sectional views sectioned from different sections. As illustrated in FIGS. 4A-4D, the needle seat 32 is a substantially hollow cylindrical needle seat body; a base seat 38 is provided at the proximal side of the needle seat body; a diameter tapered portion 33 is provided at a distal side of the needle seat body, and an elastic arm 35 spreading radially outwardly is also provided on the needle seat body. The figure shows two elastic arms 35. However, those skilled in the art may understand that the number of elastic arms 35 can also be one or more than two, as long as they cooperate with corresponding portions of the handle 20; besides, a cylinder of the needle seat body of the needle seat 32 is preferably cylindrical, but may also be other prismoids.

Figure 4A:
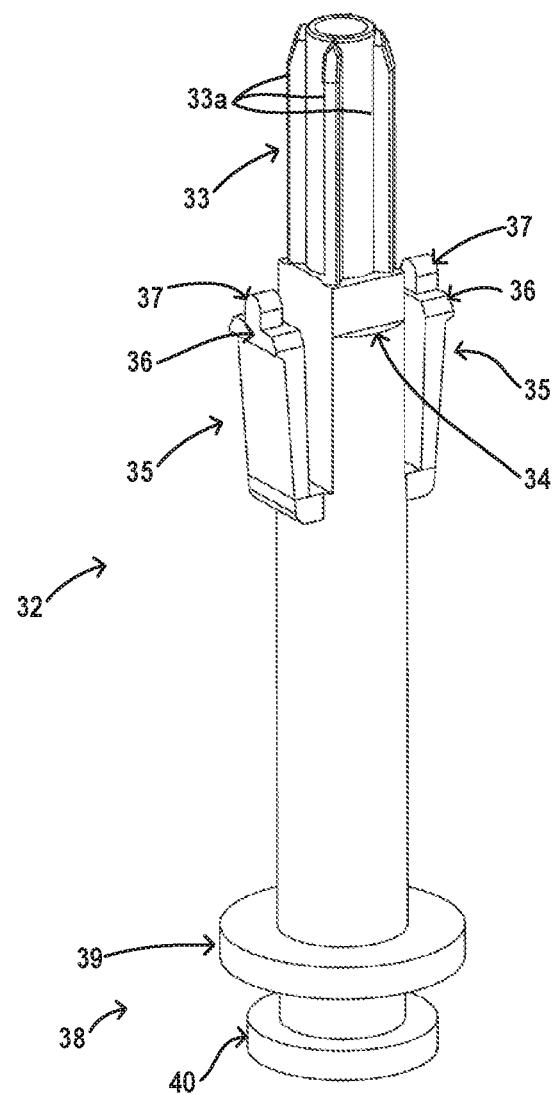
FIGS. 4A, 4B, 4C and 4D are stereoscopic diagrams of a needle seat of the retaining needle according to the first embodiment illustrated in FIGS. 1A and 1B and longitudinal sectional views sectioned from different sections.
Figure 4B:
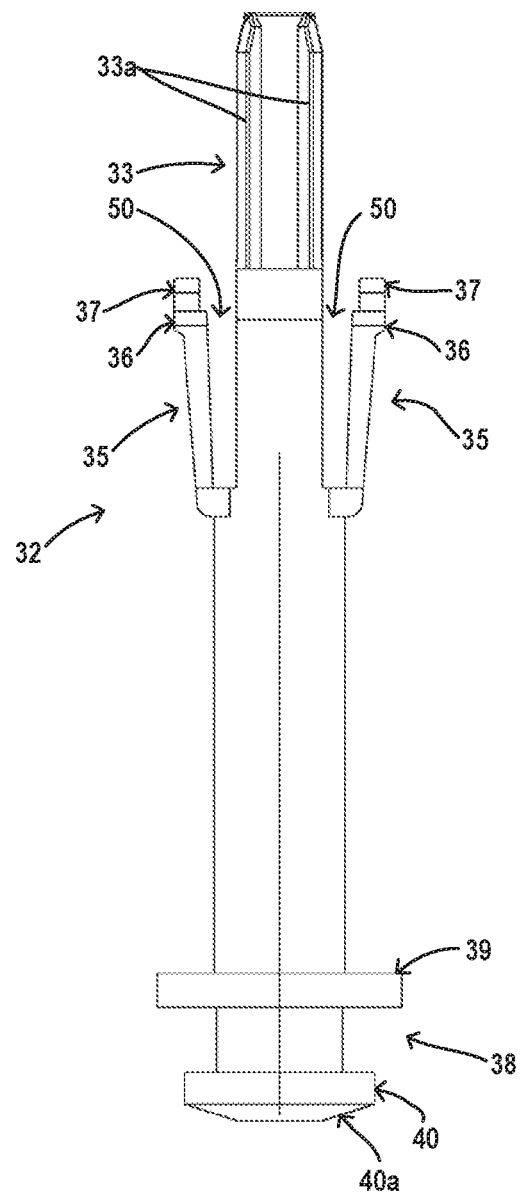
Figure 4C:
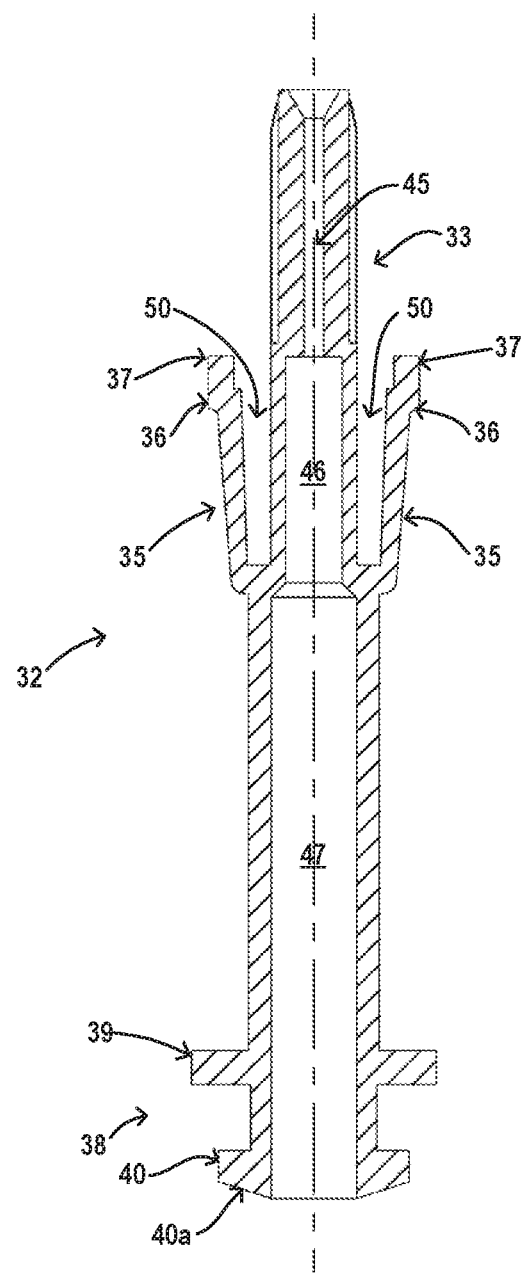

As clearly seen in FIG. 4A and FIG. 4B, a plurality of ribs or tendons 33a are provided surrounding the diameter reduced portion 33 of the needle seat 32. The number of ribs or tendons 33a corresponds to, or is less than, the number of notches 26a of a patterned hole 26. Moreover, the diameter reduced portion 33 is formed with a shoulder 34 relative to other portions of the needle seat body. The base seat 38 of the needle seat 32 is two flanges 39 and 40 stretching out radially from the needle seat body. Diameters of the flanges 39 and 40 are sized as long as they can be assembled within the handle 20; moreover, although FIGS. 4A and 4B show that the diameter of the flange 39 is greater than the diameter of the flange 40, those skilled in the art may understand that relative size relationships of the diameters of the two flanges 39, 40 are not limited, and the diameter of the flange 39 may be smaller than that of the flange 40. The flange 40 may form an oblique face 40a at a bottom side so as to facilitate assembly of a vacuum sealing plug 120 (see FIGS. 2A, 2B and 7). The elastic arm 35 of the needle seat 32 spreads radially outwardly from the needle seat body and reserves enough gap 50 between the elastic arm 35 and the needle seat body. Those skilled in the art may understand that the gap 50 may be formed because the wall thickness of the needle seat body is thinned here such that a larger gap 50 is formed between the needle seat body and the elastic arm (as shown in FIGS. 4B and 4C), or because the elastic arm 35 spreads outward with a enough large size. As illustrated in FIGS. 4A and 4B, the elastic arm 35 spreads radially outwardly from the needle seat body and extends in a direction from the proximal side to the distal side; a boss-shaped snap part 36 radially outwardly is provided at the distal side of the elastic arm; and an end head 37 is provided at an end. As shown in the figure, the end head 37 is a rounded small bulge. Those skilled in the art will appreciate that the end head 37 may also assume a shape as a trapezoid. Compared with the width of the arm body of the elastic arm 35, the width of the end head 37 is relatively smaller. As will be depicted hereinafter, this facilitates the extruding arm of the button of the safety mechanism 100 to pass through the gap 50 more quickly.

Figure 4D:
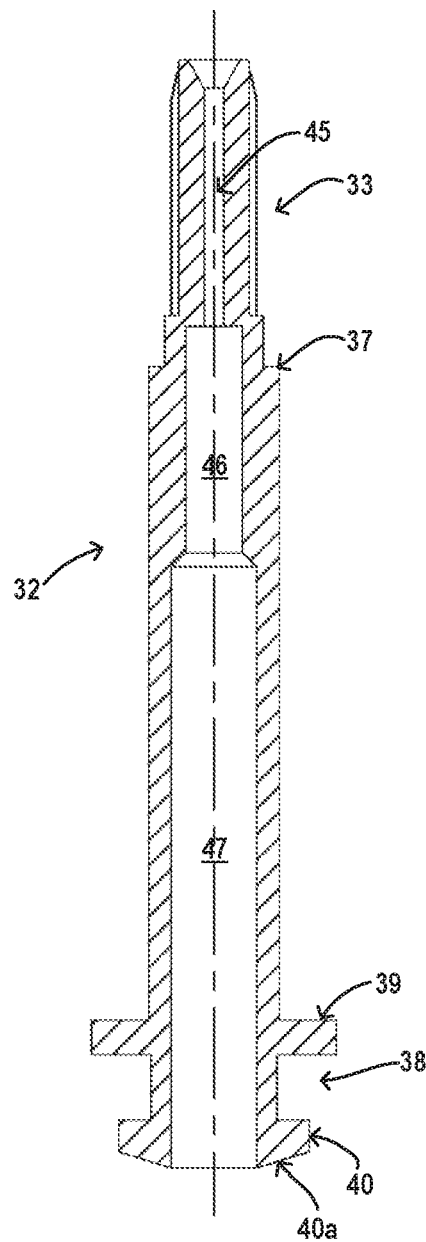

Besides, as most clearly seen in FIGS. 4C and 4D, the needle seat 32 is hollow and has a through lumen. FIGS. 4C and 4D show that the lumen in the needle seat 32 is divided into a plurality of segments, wherein a distal side segment lumen 45 at a diameter reduced portion 33 of the needle seat 32 is used for receiving and fixing the puncture needle 31, such that the lumen of the hollow puncture needle 31 is in communication with the middle-segment lumen 46 and the proximal side segment lumen 47 of the needle seat 32, such that after the puncture needle 31 punctures into the blood vessel, the blood can flow into the middle-segment lumen 46 and the proximal side segment lumen 47 of the needle seat 32, so as to prompt the user. The proximal end of the needle seat 32, i.e., the base seat 38 side, is blocked by a choke plug 48 (see FIGS. 2A and 2B) so as to prevent blood from flowing out.

When the needle and needle seat assembly 30 is assembled with the handle 20, the diameter tapered portion 33 of the needle seat 32 passes through a patterned hole 26 on the distal end 25 of the handle distal side portion 23; ribs or tendons 33a of the diameter reduced portion 33 reaches into corresponding notches 26a of the patterned hole 26, which may prevent rotation of the needle seat 32. Meanwhile, because a size of a shoulder 34 of the diameter reduced portion 33 formed relative to the needle seat body is larger than the size of the patterned hole 26, the needle seat 32 can be snapped at the patterned hole 26, preventing the needle seat 32 from over-reaching outside of the handle 20. The base seat 38 of the needle seat 32 is engaged with the vacuum sealing plug 120. The vacuum sealing plug 120 is a commonly-used sealing plug. In order to fit with the base set 38, the vacuum sealing plug 120, as shown in FIG. 7, is of a substantially bowl shape, whose outer diameter is interference-fitted with an inner diameter of the lumen 21 of the handle 20 (see FIGS. 9B and 10C) so as to form vacuum inside the lumen 21 of the handle 20. Therefore, the vacuum sealing plug 120 has a lumen 121 and a boss 122 protruding inwardly from an inner bowl opening of the bowl shape so as to be snap-fitted to a flange 40. For the convenience of joining, an oblique surface 123 is formed on an upper side of the boss 122.

Figure 8A:
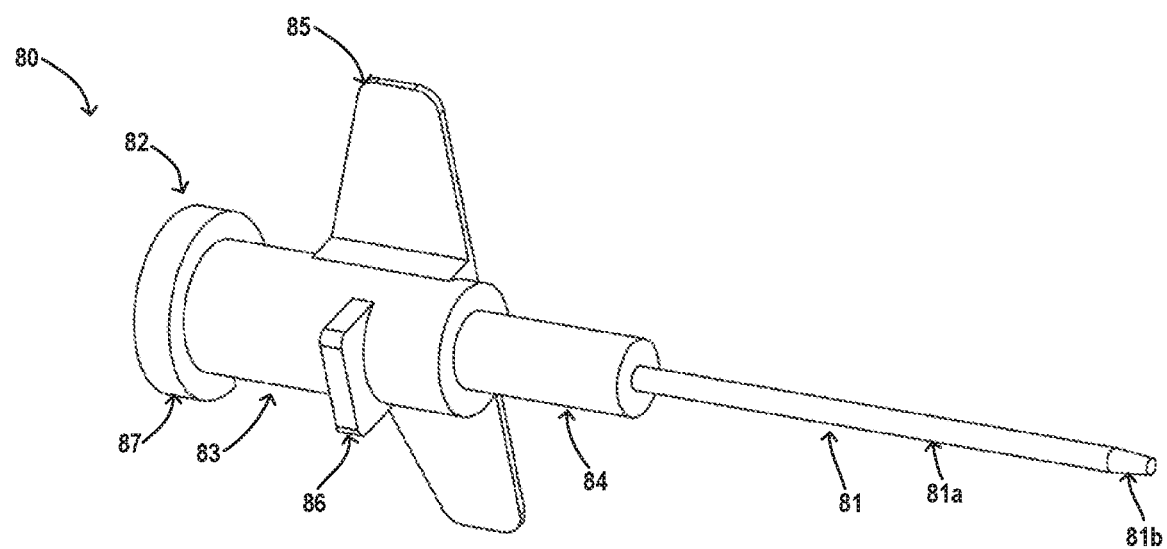
Figure 8B:
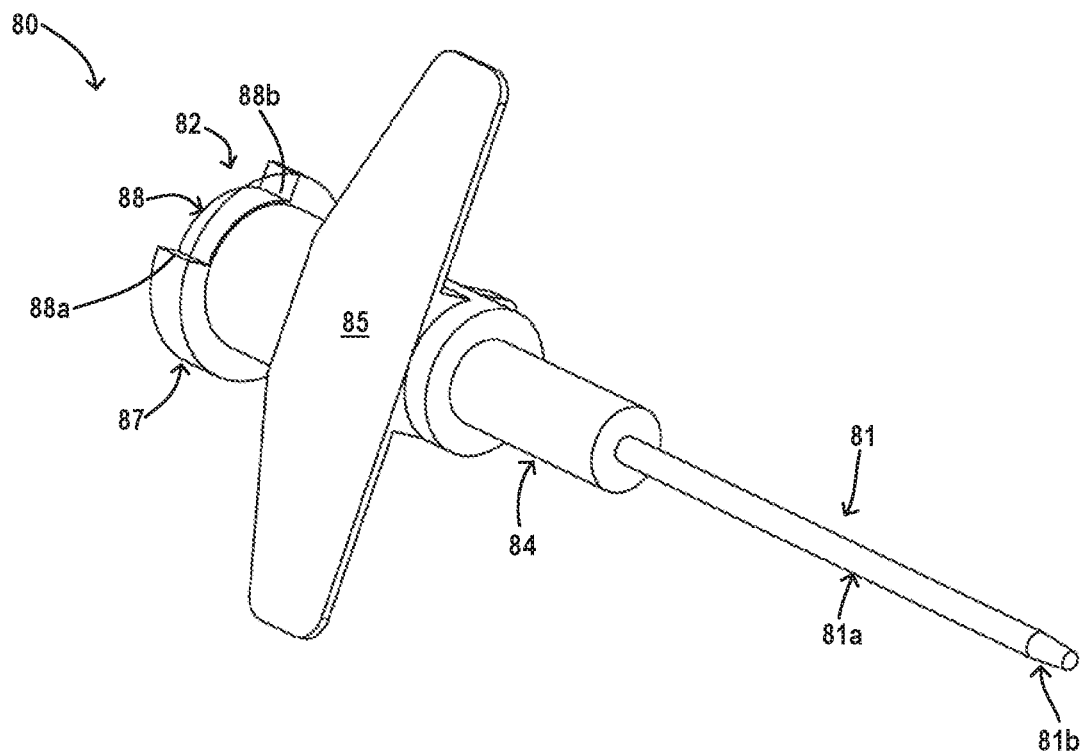
Figure 8C:
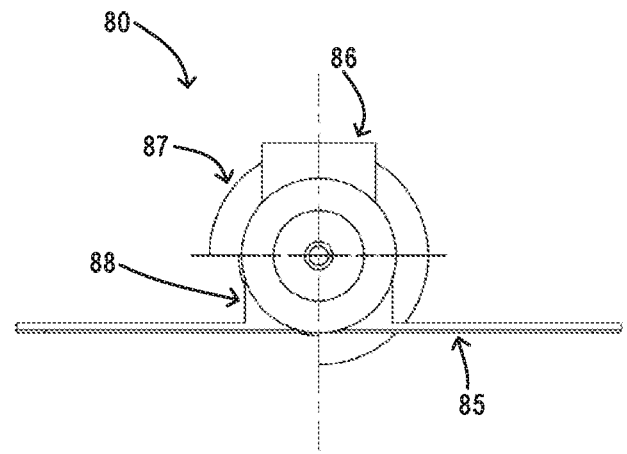
Figure 8D:
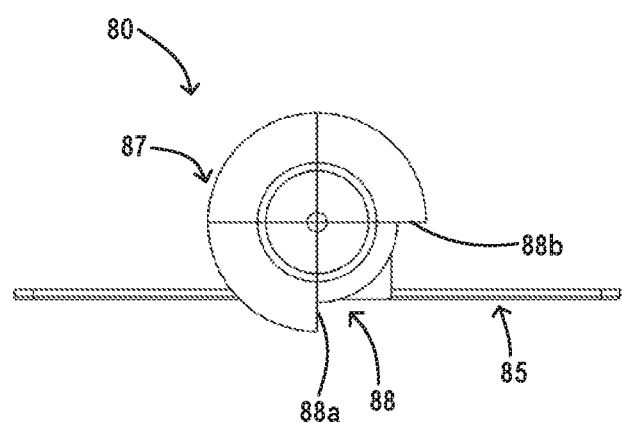
Figure 8E:
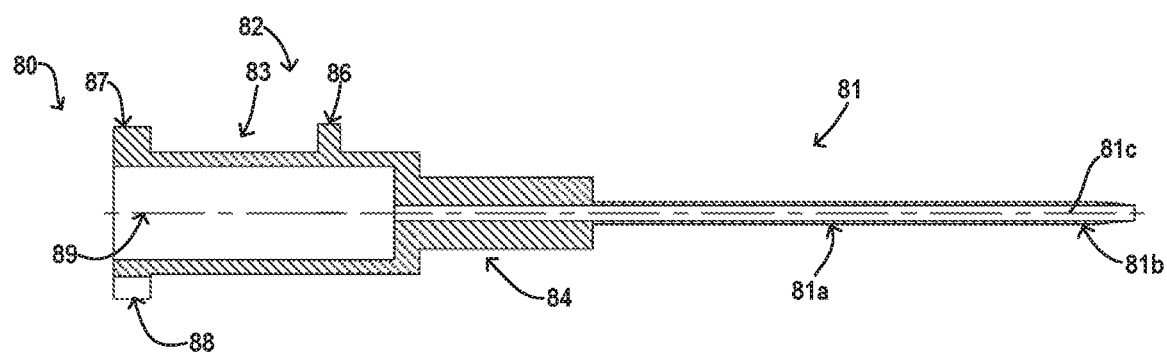

FIGS. 8A-8E are stereoscopic diagrams and longitudinal sectional views of a catheter and catheter hub assembly 80 of the retaining needle 10 according to the first embodiment illustrated in FIGS. 1A and 1B observed from different directions. The catheter and catheter hub assembly 80 comprises a catheter 81 and a catheter hub 82. The catheter 81 comprises a catheter body 81a, a tapered portion 82b located at a distal end of the catheter body 81a, and a through catheter lumen 81c. The catheter hub 82 comprises a cylindrical catheter hub body 83. A diameter reduced cylindrical catheter receiving portion 84 extending to the distal side is provided at the distal end of the cylindrical catheter hub body 83, for receiving a proximal side portion of the catheter 81. A protruding portion 86 is provided at one side of the catheter hub body 83 or upper side or at a side facing away from the patient's skin when in use, such that the user pushes the catheter and catheter hub assembly 80 to the distal side during use. A wing sheet 85 is provided at an opposite side of the protruding portion 86 or at the patient's skin side during use; when the catheter and catheter hub assembly 80 is in place, the user may press the wing sheet 85 with one hand to hold the position of the catheter and catheter hub assembly 80 while press the safety mechanism 100 with another hand, so as to retract the puncture needle 31; besides, after the retaining needle has been arranged, the wind sheet 85 (thereby causing the catheter and catheter hub assembly) is attached to the patient's skin using a medical adhesive tape. A peripheral flange 87 is provided at a proximal end of the catheter hub body 83, and a notch 88 is formed on the flange 87; the notch 88 has two sidewalls 88a and 88b. When the catheter and catheter hub assembly 80 is assembled together with the handle 20 and the needle and needle seat assembly 30, an end face of the proximate end of the catheter hub body 83 cooperates with an end face of the distal end 25 of the distal side portion 23 of the handle 20; the diameter reduced portion 33 of the needle seat 32 passes through a patterned hole 26 on the distal end 25 of the handle distal side portion 23 till reaching into the lumen 89 of the cylindrical catheter hub body 83; the puncture needle 31 reaches out from the diameter reduced portion 33 of the needle seat 32 into the catheter hub 82, and passes through the catheter lumen 81c of the catheter 81; besides a sharp tip of the puncture needle 31 projects out from a tapered tip 81b of the catheter 81; meanwhile the position of the notch 88 is aligned with the boss 29 on the end face of the distal end 25 of the distal side portion 23 of the handle 20, thereby stopping the catheter and catheter hub assembly 80 from rotating relative to the handle 20 through the cooperation of the notch 88 and the boss 29, meanwhile relative positions among respective portions are determined. Although the notch 88 as shown in FIG. 8D is a notch occupying ¼ of the circumference, those skilled in the art may understand that the size of the notch 88 is not limited thereto, as long as it can cooperate with the boss on the end face of the distal end 25 of the distal side portion 23 of the handle 20 to stop the catheter and catheter hub assembly 80 from rotation.

Besides, those skilled in the art may also understand that the assembly connection relationship between the distal side portion 23 of the handle 20 and the catheter and catheter hub assembly 80 is not limited thereto. An additional hole may be formed on the distal end 25 of the distal side portion 23 of the handle 20, while bosses are formed on the proximal end face of the catheter hub body 83; through cooperation between holes and bosses, the distal side portion 23 of the handle 20 is connected to the catheter and catheter hub assembly 80 such that although they cannot rotate, they can move relative to each other in a longitudinal direction by pushing the protruding portion 86 on the catheter hub 82.

Figure 3A:
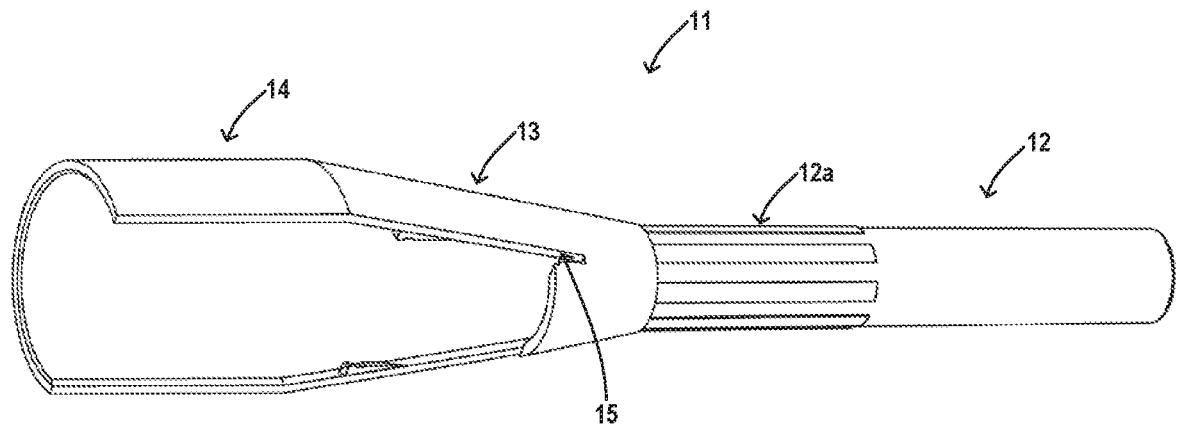
FIGS. 3A and 3B are stereoscopic views and longitudinal sectional views of a protection sheath of the retaining needle according to the first embodiment as illustrated in FIGS. 1A and 1B.
Figure 3B:
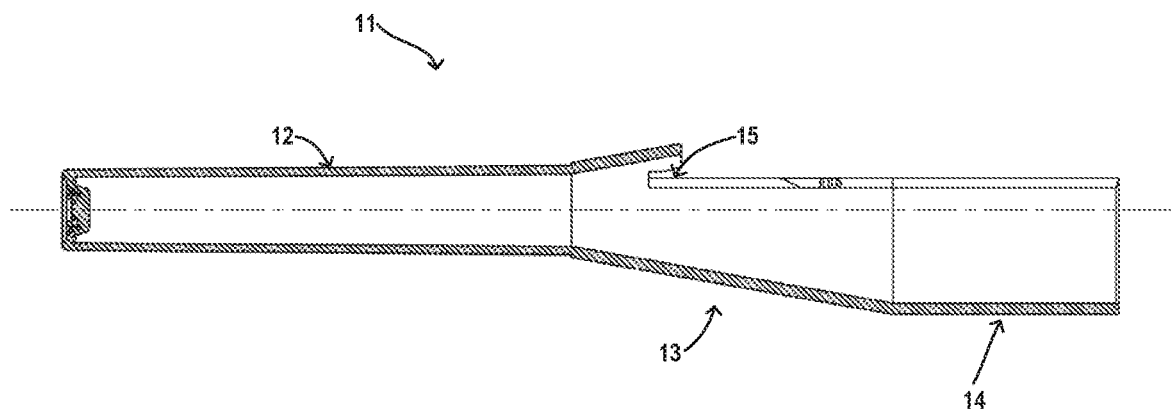

FIGS. 3A and 3B illustrate a protection sheath 11 of a retaining needle 10 of the present disclosure. A shape of the protection sheath 11 is substantially identical to the shape of the distal side portion of the retaining needle 10 (or a distal side portion of the handle 20 and the catheter and catheter hub assembly) of the retaining needle 10. The illustrated protection sheath 11 comprises a small cylindrical portion 12, a large column portion 14, and a tapered transition portion 13 therebetween. A pattern 12a may be provided on an exterior surface of the small cylindrical portion 12 so as to facilitate grabbing when removing the protection sheath 11. The large column portion 14 and the tapered transition portion 13 remove a portion of a lower side so as to be easily sleeved to the distal side portion of the retaining needle; meanwhile, a notch 15 is also reserved at the tapered transition portion 13, so as to be snapped on the wing sheet 85 of the catheter and catheter hub assembly 80. Those skilled in the art may also envisage other manners of configuring the protection sheath, as long as they can prevent the puncture needle of the unused retaining needle from puncturing a person in contact.

A safety mechanism 100 according to the first embodiment of the present disclosure comprises a snapping step 28 disposed on an inner side wall of the distal side portion 23 of the hollow handle 20; at least one elastic arm 35 disposed on the needle seat 32 and spreading radially outwardly, a tip portion of the elastic arm having a protruding snap part 36, the snap part 36 being for joining the snapping step 28; a button 110 disposed on a distal side portion 23 of the handle 20; when the button 110 is depressed, the button 110 presses the elastic arm 35 in a radially inward direction, such that the snap part 36 of the elastic arm 35 is disengaged from the snapping step 28.

FIGS. 6A, 6B, and 6C are stereoscopic diagrams and top views of a button 110 of the retaining needle 10 according to the first embodiment illustrated in FIGS. 1A and 1B. The button 110 according to the present disclosure comprises a press part 111 and at least one extruding arm 112 radially (i.e., radial of the handle 20) extending from the press part 111, wherein the number of extruding arms 112 is consistent with that of the elastic arms 35 of the needle seat 32 so as to act in mutual cooperation, thereby enhancing safety. In the examples as illustrated in FIGS. 6A-6C, the button 110 comprises two extruding arms 112. A distal end of each extruding arm 112 has a thickened portion 113. The button 110 further comprises at least one driving arm 114 extending radially (i.e., radial of the handle 20) from the press part 111. Wherein, the number of driving arms 114 is at least one, which may be less than or equal to the number of the elastic arms 35 of the needle seat 32 so as to act in mutual cooperation. In the examples as illustrated in FIGS. 6A and 6C, the button 110 comprises two driving arms 114, and the driving arm 114 is disposed exterior to the extruding arm 112. The driving arm 114 has an inclined end portion 115. When pressing the button 110, the driving arm 114 will push the elastic arm 35 along a radially inward direction, such that the elastic arm 35 is disengaged from the snapping step 28. As will be described in further detail later, those skilled in the art may understand that the driving arm 114 causes disengagement of the elastic arm 35 from the snapping step 28, while the extruding arm 112 is for further pressing the elastic arm 35 against the snapping step 28; therefore, in some embodiments, an extruding arm might not be provided to the button, with only a driving arm being provided. The elastic arm is depressed against the snapping step by virtue of its own elasticity.

FIGS. 9A, 9B, and 9C illustrate a cooperation relationship between the button and other components when the safety mechanism of the retaining needle according to the first embodiment is not depressed. FIGS. 10A-10H illustrate a cooperation relationship between the button and other members when the safety mechanism of the retaining needle according to the first embodiment is just depressed.

FIG. 9B is an enlarged view of a part within the double-dotted-line frame of FIG. 9A; and FIG. 9C is a sectional view taken along a centerline 9AA-9AA in FIG. 9B. After being assembled, the button 110 is disposed within a distal side portion 23 of the handle 20 illustrated in FIG. 5A, while the pressing part 111 of the button 110 is disposed within a button hole 27; when not being depressed, the surface of the pressing part 111 is substantially in flush with the surface of the distal side portion 23. As illustrated in FIGS. 9B and 9C, when not being depressed, the extruding arm 112 of the button 110 reaches into the gap 50 between the elastic arm 35 of the needle seat 32 and the needle seat body, and a thickened portion 113 at the end of the extruding arm 112 pushes the elastic arm 35 radially outwardly, such that the radially outward snap-step-shaped snap part 36 of the elastic arm 35 is snapped at the snapping step 28 on the inner wall of the distal side portion of the handle 20. However, when the button is not depressed, the driving arm 114 is located exterior to the elastic arm 35 (see FIGS. 9B and 9C) and is not in contact with the elastic arm 35 yet. Due to the press of the thickened portion 113 at the end of the extruding arm 112 and the elasticity of the elastic arm 35 per se, the elastic arm 35 securely abuts against the snapping step 28, so as to retain the needle and the needle seat assembly 30 at the position, and the puncture needle 31 extends out of the catheter 81.

Figure 10A:
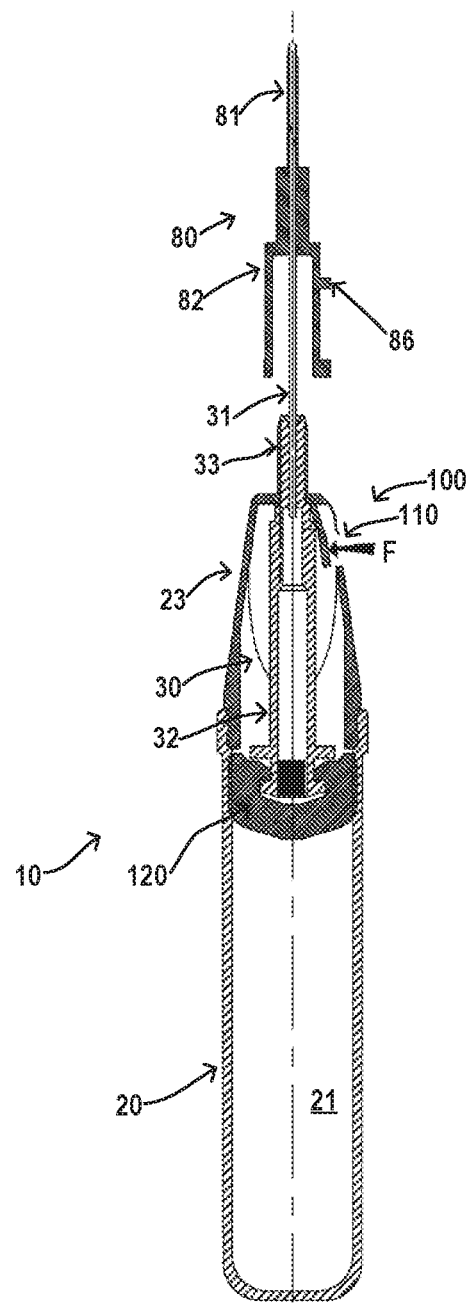
Figure 10D:
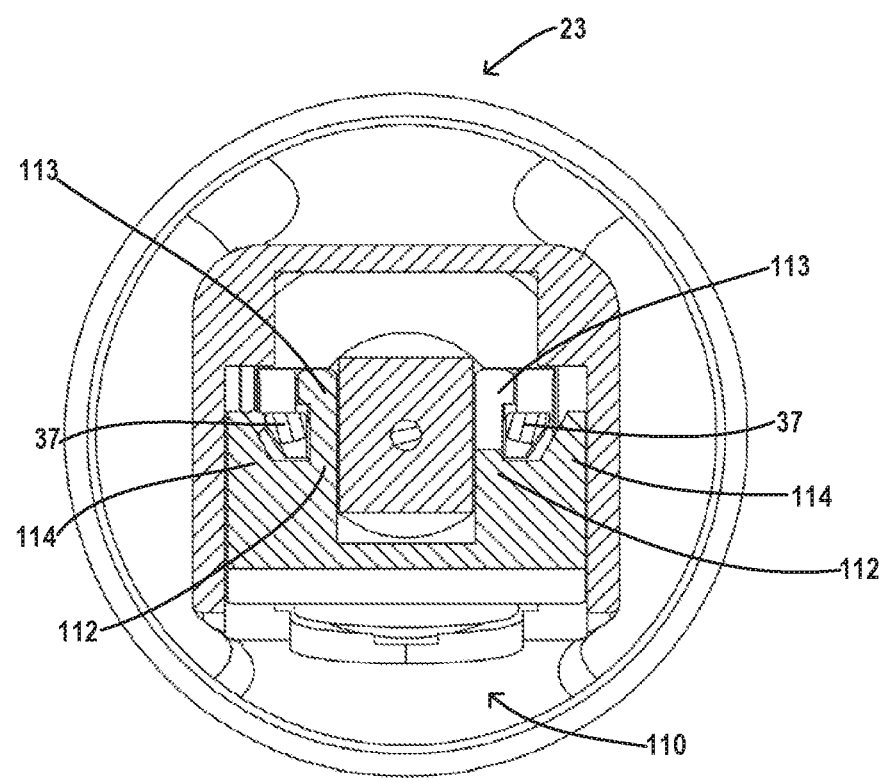
Figure 10E:
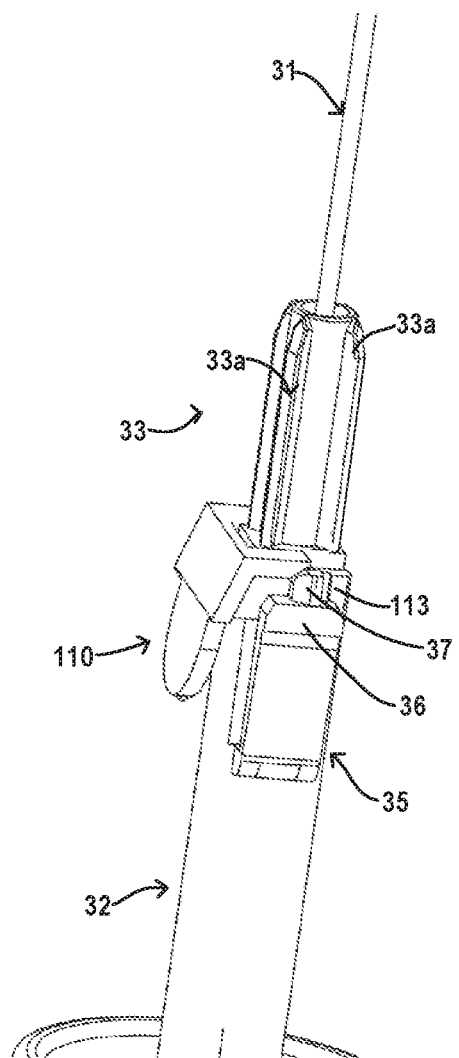
Figure 10F:
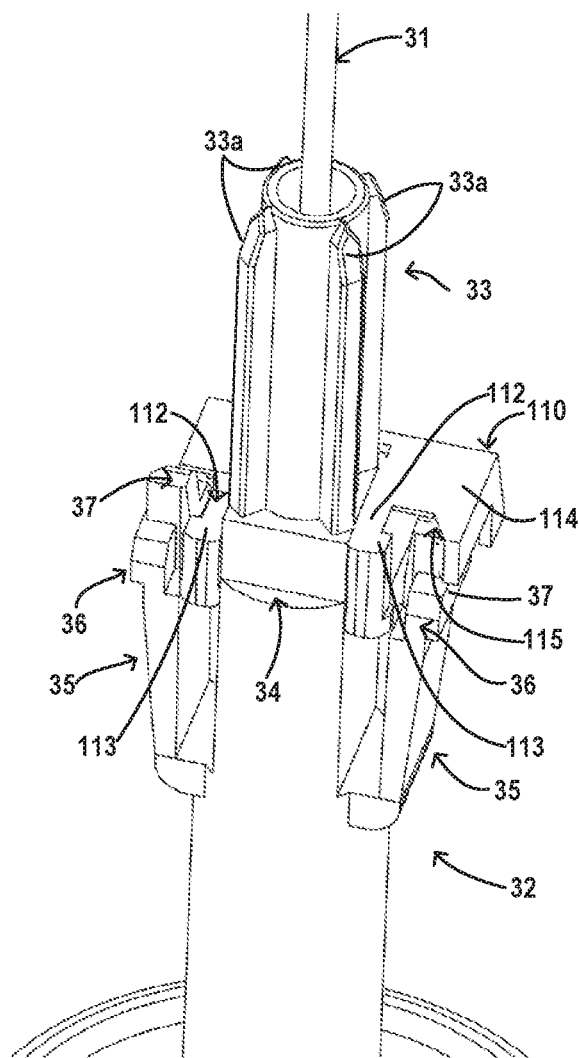
Figures 10G, 10H:
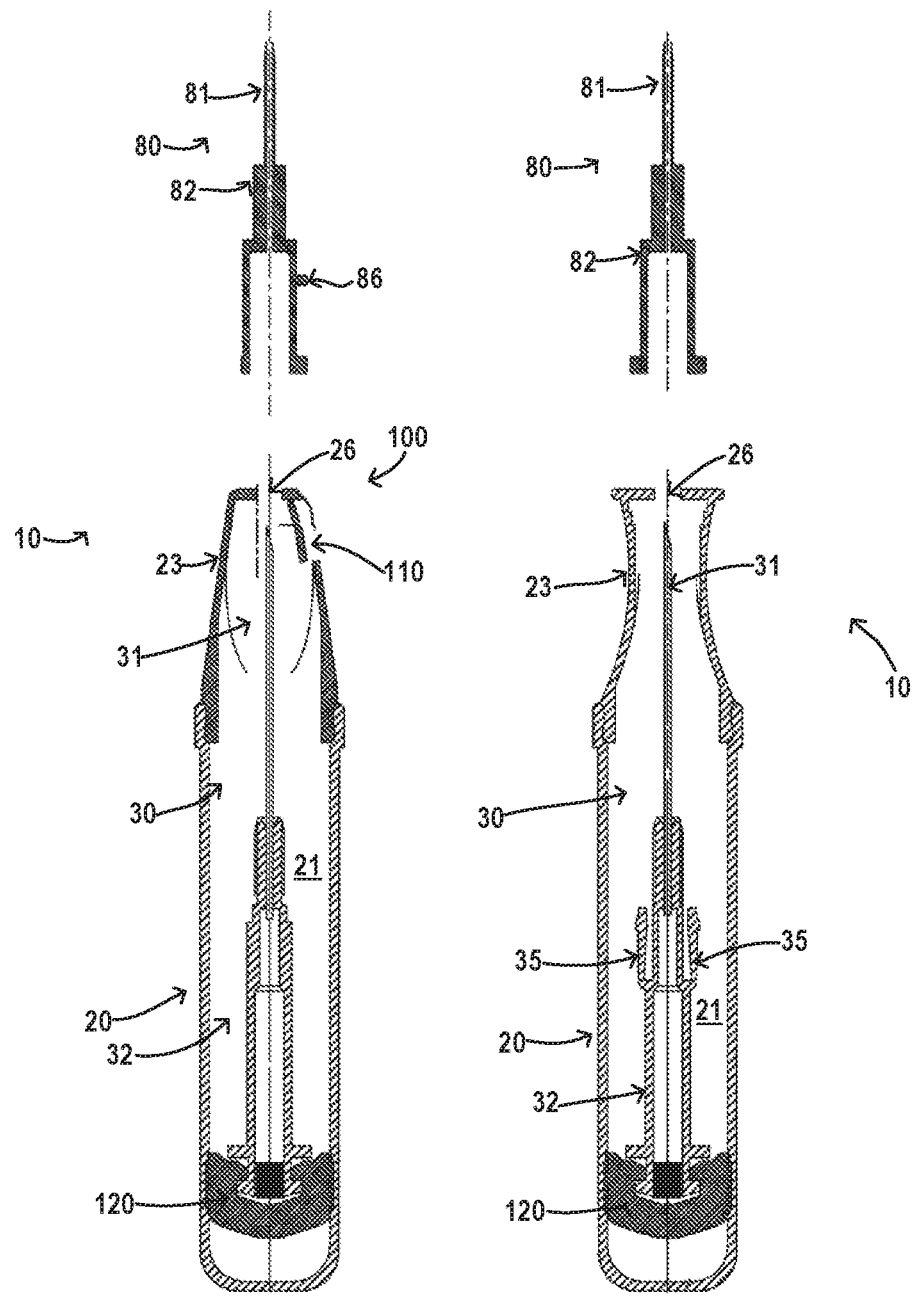

After the needle 31 and the catheter 81 are positioned duly and the catheter and catheter hub assembly 80 are advanced, and when the puncture needle 31 needs to be retracted, the safety mechanism 100 is activated, i.e., pressing down the button 110 by force (see FIG. 10A) so as to retract the puncture needle 31. More specifically, FIGS. 10C, 10D, 10E and 10F illustrate in detail the relationships among the elastic arm 35, the distal side portion 23 of the handle 20, and the button 110 when the button 110 is just depressed. Wherein, FIG. 10E only illustrates a portion of the button 110; a portion of the driving arm 114 is removed to expose the extruding arm 112 in its behind, and a portion of the upper part of the extruding arm 112 is removed to clearly show its relationship with an end head 37 of the elastic arm 35. FIG. 10F shows the same content as FIG. 10E, just observed from the other side. As illustrated in FIG. 10C-FIG. 10F, after the button 110 is depressed, the extruding arm 112 of the button 110 moves forward, and the thickened portion 113 previously abutting against the elastic arm 35 moves through the gap 50 beyond the end head 37 of the elastic arm 35 (as clearly seen in FIG. 10D, FIG. 10E, and FIG. 10F) (the thickness of the end head 37 of the elastic arm 35 is smaller than the width of the body portion of the elastic arm 35, which facilitates the thickened portion 113 to pass through the gap 50 quickly). Because the portions of the extruding arm 112 except the thickened portion 113 have a smaller thickness, the elastic arm 35 will not be radially outwardly extruded to the snapping step 28; the elastic arm 35 bounces back inwardly due to its own elasticity and is disengaged from the snapping step 28. On the other hand, because the driving arm 114 is disposed exterior to the elastic arm 35, both the extruding arm 112 and the driving arm 114 move forward as the button 110 is depressed; the inclined end part 115 of the driving arm 114 then approaches to the end head 37 of the elastic arm 35, and the inclined side of the inclined end part 115 gradually pushes the elastic arm 35 to move radially inwardly, thereby assisting the snap part 36 of the elastic arm 35 in disengaging from the snapping step 28. Because the elastic arm 35 is disengaged from the distal side portion 23 of the handle 20, while the lumen 21 of the handle 20 is vacuum inside, the needle and needle seat assembly 30 is retracted within the lumen 21 of the handle 20, as illustrated in FIG. 10G and FIG. 10H.

FIGS. 11A and 11B are stereoscopic diagrams of an unused retaining needed 10' observed from different functions according to a second embodiment of the present disclosure. FIGS. 12A and 12B are longitudinal sectional views of the retaining needle according to the second embodiment as illustrated in FIGS. 11A and 11B sectioned from different sections, wherein the structures and configurations of the proximal side portion of the handle 20' and the catheter and catheter hub assembly 80' are identical to the first embodiment of the present disclosure. Here, identical parts will not be detailed. Only different features are described.

FIGS. 13A, 13B, and 13C are stereoscopic views and sectional views of a protection sheath 11' of the retaining needle 10' according to a second embodiment as illustrated in FIGS. 11A and 11B. Similarly, the shape of the protection sheath 11' is also substantially identical to the shape of a distal side portion of the retaining needle 10' (or the distal side portion of the handle 20' and the catheter and catheter hub assembly), and a lower side of the protection sheath 11' has a portion to be removed so as to be sleeved to the distal side portion of the retaining needle 10', and a notch 15' is also reserved on the protection sheath 11' so as to be snapped onto a wing 85' of the catheter and catheter hub assembly 80'.

Hereinafter, the distal side portion of the handle of the retaining needle, the needle seat, and the button of the safety mechanism according to the second embodiment will be described specifically.

FIGS. 14A, 14B, 14C, and 14D are stereographic diagrams of the needle seat 32' of the retaining needle 10' according to the second embodiment illustrated in FIG. 11A and FIG. 11B and longitudinal sectional views sectioned from different directions. Similarly, the needle seat 32' likewise has a needle seat body of a substantially hollow column, and a diameter reduced portion 33' is provided at a distal side of the needle seat body, and an elastic arm 35' radially spreading outward is also provided on the needle seat body. Two elastic arms 35' are illustrated in these figures. However, those skilled in the art may understand that the number of elastic arms 35' may be one or more than two as long as they can cooperate with corresponding parts of the handle 20'', and the column of the needle seat body of the needle seat 32' is preferably a cylinder but may also be other kinds of prismoids.

Figures 14A, 14B:
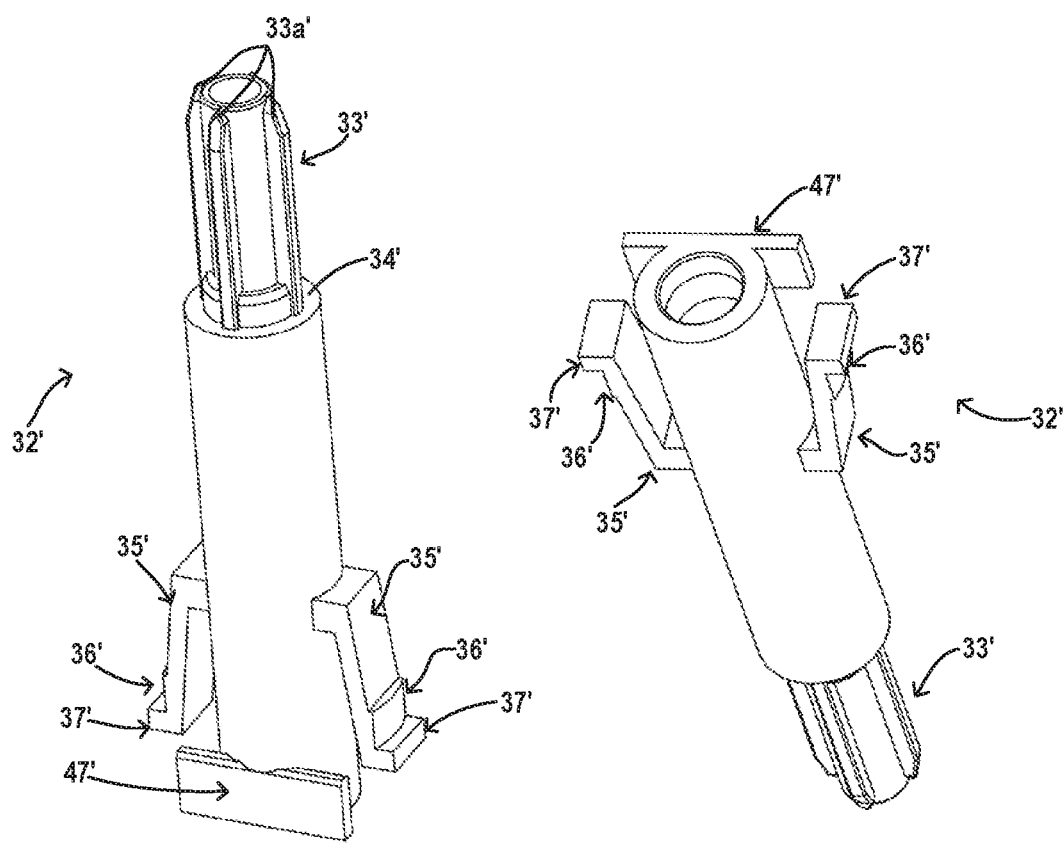

As clearly seen in FIGS. 14A and 14B, a plurality of ribs or tendons 33a' are provided at a periphery of a diameter reduced portion 33' of the needle seat 32', the number of ribs or tendons 33a' being corresponding to or less than the number of notches 26a' of a patterned hole 26'. Besides, the diameter reduced portion 33' forms a shoulder 34' relative to the needle seat body. The elastic arm 35' of the needle seat 32' spreads radially outwardly from the needle seat body and reserves an enough gap 50' between the elastic arm 35' and the needle seat body. Those skilled in the art may understand that the gap may be formed because the elastic arm 35' spreads out radially with a large size, as illustrated in FIGS. 14A, 14B, and 14D, or because the wall thickness of the needle seat body is thinned here such that a larger interstice is formed relative to the elastic arm. The elastic arm 35' spreads radially outwardly from the needle seat body and extends from a distal side to a proximal side direction; a snap part 36' is provided at a distal side of the elastic arm; the snap part 36' has a radially outward protrusion 37'. Besides, a snap-fit sheet 47' is provided at one side of the needle seat body at the proximal end of the needle seat 32'.

Figure 14C:
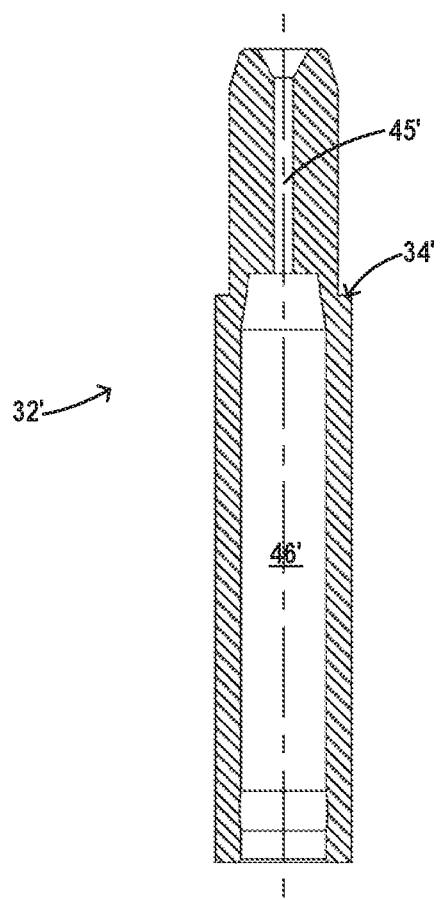
Figure 14D:
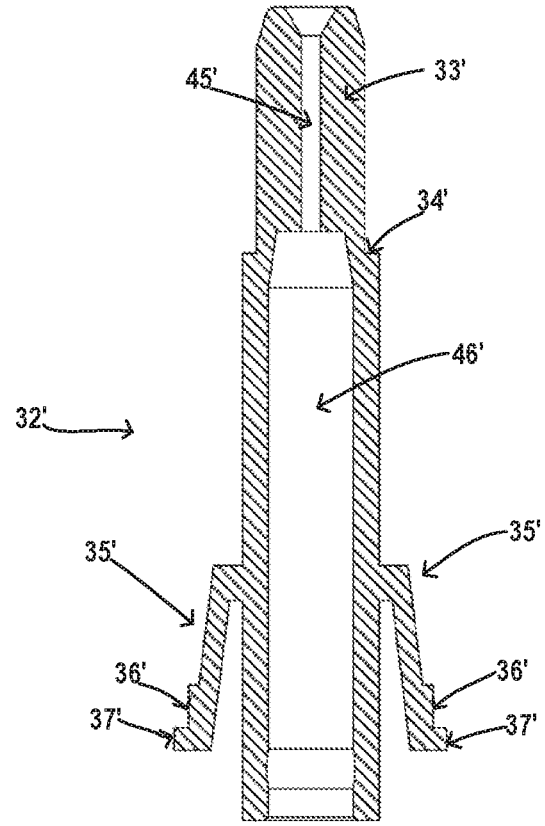

Besides, as most clearly seen in FIGS. 14C and 14D, the needle seat 32' is hollow and has a through lumen. The through lumen is divided into two segments, wherein a distal side segment lumen 45' at a diameter reduced portion 33' of the needle seat 32' is for receiving and fixing a puncture 31', such that the lumen of the hollow puncture needle 31' is in communication with the proximal side segment lumen 46' of the needle seat 32', such that blood can flow into the proximal side segment lumen 46' of the needle seat 32' after the puncture needle 31' punctures into the blood vessel, so as to prompt to the user.

FIGS. 15A, 15B, 15C, 15D, and 15E are stereoscopic diagrams of a base seat 38' of the needle seat 32' of the retaining needle 10' according to the second embodiment as illustrated in FIGS. 11A and 11B and sectional views sectioned from different directions. The base seat 38' comprises an upper disc 39', a lower disc 40', and a column segment 41' that connects the upper disc 39' and the lower disc 40'. A plunger 43' is eccentrically provided on the upper surface of the upper disc 39', on which is also provided at least one snap-fit sheet 42'. Two snap-fit sheets 42' are illustrated in the figure. The lower disc 40' may be provided with an inclined part 40a' so as to be assembled with a vacuum sealing plunger. Besides, a lower surface of the upper disc 39' may also be provided with a reinforcing tendon or rib 44'. As illustrated in FIGS. 12A and 12B, when the needle seat body of the needle seat 32' is assembled together with the base seat 38', the plunger 43' blocks the proximal end of the lumen of the needle seat 32' to block leakage of the blood flowing into the proximal side segment lumen 46' of the needle seat 32'. The snap-fit sheet 47' of the needle seat body of the needle seat 32' and the snap-fit sheet 42' of the upper disc 39' of the base seat 38' are mutually snap-fitted so as to prevent the needle seat body of the needle seat 32' from moving relative to the base seat 38'.

The safety mechanism 100' according to the present disclosure comprises a snapping step 28' on the inner side wall of the distal side portion 23' of the hollow handle 20'; a least one elastic arm 35' spreading radially outwardly disposed on the needle seat 32', an end portion of the elastic arm having a protruding snap-fit portion 36', the snap-fit portion 36' being for joining the snap-step 28'; a button 110' provided on the distal side portion 23' of the handle 20', such that when pressing down the button 110', the button 110' will push the elastic arm 35' radially inwardly, causing the snap-fit part 36' of the elastic arm 35' to be disengaged from the snap-step 28'.

FIGS. 16A and 16B are stereoscopic diagrams of a button 110' of a retaining needle 10' according to the second embodiment as illustrated in FIGS. 11A and 11B. The button 110' according to the present disclosure comprises an arc sheet-shaped pressing part 111' and at least one driving arm 114' extending from a lower part of the pressing part 111'. Wherein, the number of the driving arms 114' is identical to the number of the elastic arms 35 of the needle seat 32 so as to act in mutual cooperation. In the examples as illustrated in FIGS. 16A and 16B, the button 110' comprises two driving arms 114', and the driving arm 114' has an inclined end portion 115'. Besides, the pressing part 111' of the button 110' further has a joining part 112' for joining a receiving part 25a' of the distal side portion 23' of the handle 20'. Two joining portions 112' are shown in the figures, wherein a positioning protrusion 112a' is provided on one joining part 112' thereof. However, those skilled in the art may understand that the joining part may be at least one and may also be of other shape, as long as the button 110' is joined to a receiving part of the distal side portion 23' of the handle 20'.

FIGS. 17A and 17B are stereoscopic diagrams of a distal side portion 23' of a handle 20' of a retaining needle 10' according to the second embodiment as illustrated in FIGS. 11A and 11B. Similarly, the distal side portion 23' has an open proximal end 24' for joining an open distal end of the proximal side portion 22'. Moreover, a patterned hole 26' is provided on the distal end 25' of the distal side portion 23'; as illustrated in FIGS. 17A and 17B, a plurality of notches 26a' are formed on the patterned hole 26'. Of course, as previously mentioned, the shape of the patterned hole 26' is not limited thereto, as long as it can cooperate with a corresponding portion of the needle seat. Besides, a button hole 27' for receiving a button 110' of the safety mechanism 100' is provided on a side wall of the distal side portion 23'. An inwardly protruding snapping step 28' (see FIG. 17A) is provided on the inner wall of the distal side portion 23', the snapping step 28' being for joining the elastic arm 35' of the needle seat 32'. Besides, in order to join the catheter and catheter hub assembly 80', bulges 29' extending to a distal side are also formed on an end face of the distal end 25' of the distal side portion 23' of the handle 20' (i.e., the end face formed with the patterned hole 26') (see FIGS. 17A and 17B).

When the catheter and catheter hub assembly 80', the handle 20', and the needle and needle assembly 30' are assembled together, an end face of the proximal end of the catheter hub body 83' cooperates with an end face of a distal end 25' of the distal side portion 23' of the handle 20'; the diameter reduced portion 33' of the needle seat 32' passes through the patterned hole 26' on the distal end 25' of the distal side portion 23' of the handle till reaching into a lumen of the cylindrical catheter hub body 83'; the puncture needle 31' projects out of the diameter reduced portion 33' of the needle seat 32', entering into the catheter hub 82' and passing through the catheter lumen 81c' of the catheter 81'; besides, a sharp end of the puncture needle 31' projects out of the tapered end 81b' of the catheter 81', and meanwhile, a position of the notch 88' is aligned to the bulge 29' on an end face of the distal end 25' of the distal side portion 23' of the handle 20'; the button 110' is placed within the distal side portion 23' of the handle 20', wherein the press portion 111' of the button 110' is fitted into the button hole 27' of the distal side portion 23', and when being not depressed, the surface of the press portion 111' is in flush with two side edges of the distal side portion 23'. The snap-fit part 36' of the elastic arm 35' of the needle seat 32' abuts against the snapping step 28' on the inner wall of the distal side portion 23'.

After the puncture needle 31' and the catheter 81' are positioned and the catheter and catheter hub assembly 80' are advanced, the safety mechanism 100' is initiated when it is needed to retract the puncture needle, i.e., pressing the button 110', so as to retract the puncture needle 31. FIGS. 18A-18F are status diagrams of the retaining needle in use according to the second embodiment as illustrated in FIGS. 11A and 11B, wherein FIG. 18A illustrates a retaining needle 10' without removal of the protection sheath 11' illustrated in FIG. 18A; FIG. 18B illustrates a retaining needle 10' with removal of the protection sheath 11'; FIG. 18C illustrates a retaining needle 10' that drives the catheter and the catheter hub assembly 80' to the distal side; FIG. 18D illustrates a retaining needle 10' with the button 110' of the safety mechanism 100' being depressed; FIGS. 18E and 18F illustrate a retaining needle 10' with the puncture needle 31' in a being retracted state and in an already retracted state. FIGS. 19A and 19B are views of mutual interaction between a driving arm of the button and the elastic arm of the needle seat when the button of the retaining needle is depressed according to the second embodiment as illustrated in FIGS. 11A and 11B. When the button 110' is depressed, the driving arm 114' of the button 110' disposed exterior to the elastic arm 35', by virtue of an inclined end part 115', extrudes radially inwardly the elastic arm 35' against which the snapping step 28' on the inner wall of the distal side portion 23' abuts and pushes it away from the snapping step 28' (as illustrated in FIGS. 19A and 19B). Afterwards, the elastic arm 35' has been disengaged from the snapping step 28' and extruded inwardly by the driving arm 114'; by virtue of the vacuum action of the lumen 21' of the handle 20', the needle 32' is retracted within the handle 20'.

FIG. 20 illustrates a stereoscopic diagram of an unused retaining needle 10' with removal of the protective sheath according to a third embodiment of the present disclosure. FIGS. 21A and 21B are longitudinal sectional views of an unused retaining needle 10" sectioned from different sections according to a third embodiment of the present disclosure. Wherein, the structures and configuration of the proximal side of the handle 20" and the catheter and catheter hub assembly 80" are identical to those in the first and second embodiments of the present disclosure. Here, the identical parts will not be detailed. Only different features are described.

Hereinafter, a distal side portion of a handle of a retaining needle, a snap sleeve of the handle, a needle seat, and a button of a safety mechanism according to the third embodiment will be described in detail.

FIGS. 22A, 22B, and 22C are stereoscopic diagrams of a needle seat 32" of a retaining needle 10' according to the third embodiment as illustrated in FIG. 20 and longitudinal sectional views sectioned from different sides. Similarly, the needle seat 32" likewise has a substantially hollow column needle seat body, a diameter reduced portion 33" is provided at a distal side of the needle seat body, and on the needle seat body is also provided an elastic arm 35" spreading radially outwardly. One elastic arm 35" is shown in the figures. However, those skilled in the art may understand that the number of elastic arms 35" may be one or more than two, as long as they can cooperate with corresponding portions of the handle 20"; and the column of the needle seat body of the needle seat 32" is preferably a cylinder but may also be other kinds of prismoids.

As clearly seen in FIG. 23a, a plurality of ribs or tendons 33a" are provided at a periphery of the diameter reduced portion 33" of the needle seat 32"; the number of ribs or tendons 33a" is corresponding to or less than the number of notches 26a" of a pattern hole 26" on a distal end face of a distal side portion 23" of a handle 20". Moreover, the diameter reduced portion 33" forms a shoulder 34" relative to the needle seat body. The elastic arm 35" of the needle seat 32" spreads radially outwardly from the needle seat body and an enough gap 50" is reserved between the elastic arm 35" and the needle seat body. Those skilled in the art may understand that the gap may be formed because the elastic arm 35" spreads outwardly with a large size, as illustrated in FIG. 23A. A large gap may be formed from the elastic arm because the wall thickness of the needle seat body is thinned here. The elastic arm 35" spreads radially outwardly from the needle seat body and extends from the distal side to the proximal side; a snap-fit part 36" is provided at a distal side of the elastic arm; the snap-fit part 36" has a snap-step 36a" protruding radially outwardly and a wedge-shaped part 37" longitudinally extending from the snap-step 36a".

FIG. 24 illustrates a sectional view of a needle seat base seat 38" of the retaining needle 10' according to the third embodiment as illustrated in FIG. 20. The base seat 38" comprises an upper disk 39", a lower disc 40", and a column segment 41" connecting the upper disc 39" and the lower disc 40". An upper surface of the upper disc 39" is concentrically provided with a plunger 43". The lower disc 40" may be provided with an inclined part 40a" so as to be assembled with the vacuum sealing plug. As illustrated in FIGS. 21A and 21B, when the needle seat body of the needle seat 32" is assembled with the base seat 38", the plunger 43" blocks a proximal end of a lumen of the needle seat 32" to stop leakage of the blood flowing into the proximal side segment lumen 46" of the needle seat 32".

As illustrated in FIGS. 21A and 21B, the handle 20" further comprises a snap sleeve 20a" for snap-fitting with the snap-fit part 36" of the elastic arm 35". The snap sleeve 20a" shown in FIG. 21A is of a cylindrical structure disposed within the handle 20"; a cylinder bottom is disposed at a proximal end of the handle 20", while an open end faces the needle seat 32" for receiving the needle seat 32"; vacuum is formed in the snap sleeve 20a" by the vacuum sealing plug 120". Moreover, an edge 20a*l*" of the snap sleeve 20a" is snap-fitted with the snapping step 36a" (see FIG. 25). Of course, the form of the snap sleeve 20a" is not limited thereto, which may also be a segment of cylinder with both ends being open, for example disposed within a proximal side portion of the handle 20", and vacuum is still formed by the lumen 21" of the handle 20".

FIGS. 23A and 23B are stereoscopic diagrams of a handle distal side portion 23" of a retaining needle 10" according to the third embodiment as illustrated in FIG. 20. The distal side portion 23" of the handle 20" is similar to that in the first embodiment, but the button 110" is formed by a part of side wall of the distal side portion 23", such that it can be depressed radially inwardly by means of a hinge part 111a" formed between the distal end face and the side wall of the distal side portion 23", thereby pushing the snap-fit part 36" of the elastic arm 35" inwardly to be disengaged from the snap sleeve 20a".

FIG. 25 is an enlarged view of a part of FIG. 21A, which illustrates a cooperation relationship among the button 110", the elastic arm 35" of the needle seat 32", and the snap sleeve 20a". When the safety mechanism 100" is not depressed, the diameter reduced portion 33" of the needle seat 32" disposed within the handle 20" extends out from a patterned hole 26" on a distal side end face of the distal side portion 23" of the handle 20" and is snapped at the shoulder 34"; the elastic arm 35" of the needle seat 32" spreads radially outwardly and is snap-fitted at an edge 20a*l*" of the snap sleeve 20a" through the snap-step 36a"; the base seat 38" of the needle seat 32" is joined with the vacuum sealing plug 120"; vacuum is formed in the snap sleeve 20a". After the puncture needle 31" and the catheter 81" are positioned and the catheter and catheter hub assembly 80" are advanced, the safety mechanism 100" is initiated when it is needed to retract the puncture needle 31", i.e., pressing down the button 110" (see FIG. 25) so as to retract the puncture needle 31". When depressing the button 110", the button 110" rotates inwardly about a hinge part 111a" to push the elastic arm 35" radially inwardly, such that 35" moves radially inwardly; the snapping step 36a" is disengaged from the edge 20a1" of the snap sleeve 20a"; by virtue of vacuum, the needle seat 32" and the puncture needle 31" are retracted into the snap sleeve 20a", as shown in FIG. 26.

FIG. 26 is a sectional view of the puncture needle of the retaining needle according to the third embodiment of the present invention as illustrated in FIG. 20 which is retracted within the handle after the button is depressed.

FIGS. 27A, 27B, and 27C illustrate a fourth embodiment of the present disclosure, which are a sectional view of the retaining needle 10''', a sectional view of a needle seat base seat 38''', and a sectional view of the O-shaped sealing ring according to the fourth embodiment, respectively.

The structure of the fourth embodiment of the present disclosure is substantially identical to that of the third embodiment, except the structure of the base seat 38''' of the needle seat. As illustrated in FIG. 27B, the base seat 38''' of the needle seat 32''' is a cylinder, and a segment of small cylinder 39''' protrudes out of an upper surface of the cylinder to block a proximal end of the needle seat 32'''. A plurality of channels 40''' are formed at a periphery of the cylinder, for receiving an O-shaped ring 41'''. The working principle of the fourth embodiment is completely identical to the working principle of the third embodiment.

The retaining needle according to the present disclosure as described above may be made of any appropriate material, and the distal side portion and the needle seat of the handle are transparent so as to be capable of being observed by a user after the blood enters into the retaining needle.

The specific structure of the present disclosure has been described above in the preferred embodiments with reference to the accompanying drawings. However, those skilled in the art should understand that the specific depiction above is exemplary, and those skilled in the art may make various transformations and improvements according to the depiction above without departing from the scope of the present disclosure.

The invention claimed is:

1. A safety mechanism for a retaining needle, the retaining needle comprising a hollow handle and a needle seat at least partially disposed within the handle for receiving a puncture needle, characterized in that the safety mechanism comprising: a snapping step disposed at an inner side of the hollow handle; at least one elastic arm radially spreading outward disposed on the needle seat, an end portion of the elastic arm has a snapping portion radially protruding outward, the snapping portion being engaged with the snapping step; and a button disposed on a distal side portion of the handle, the button, when being depressed, pushing the elastic arm along a radial inward direction, such that while the snapping portion of the elastic arm is disengaged from the snapping step, the needle seat and the puncture needle stretching outside of the handle are retracted into the hollow handle by virtue of vacuum within the hollow handle, wherein the button comprises a pressing portion and at least one extruding arm radially extending from the pressing portion, an end of the extruding arm having a thickened portion, wherein, when the button is not depressed, the extruding arm reaches into a gap between a body of the needle seat and the elastic arm spreading outward radially from the body and presses the elastic arm against the snapping step using the thickened portion, and wherein, after the button is depressed, the thickened portion of the extruding arm extends beyond the gap, not radially extruding the elastic arm outwardly anymore.

2. The safety mechanism for a retaining needle according to claim 1, wherein the snapping step is disposed on an inner wall at the distal side portion of the hollow handle, and the elastic arm spreads outward radially and extending to a distal direction from a proximal side of the needle seat.

3. The safety mechanism for a retaining needle according to claim 2, wherein the button has at least one driving arm extending radially, the driving arm has an inclined end and is disposed at an external side of the elastic arm; after the button is depressed, an inclined side of the inclined end of the driving arm gradually extrudes the elastic arm radially inwardly.

4. The safety mechanism for a retaining needle according to claim 3, wherein the button is formed by a side wall of the distal side portion of the handle; when the button is depressed, the button pushes the snapping part of the elastic arm away from the edge of the snap sleeve.

5. The safety mechanism for a retaining needle according to claim 1, wherein the button further comprises at least one driving arm extending radially from the pressing part, the driving arm has an inclined end and is disposed at an exterior side of the extruding arm;
   when the button is not depressed, the driving arm is disposed external to an end head of the elastic arm without contacting therewith;
   after the button is depressed, as the thickened portion of the extruding arm reaches beyond the gap so as not to extrude the elastic arm outward radially, an inclined side of an inclined end of the driving arm disposed exteriorly gradually extrudes the elastic arm radially inwardly.

6. The safety mechanism for a retaining needle according to claim 1, wherein a width of an end head of the elastic arm is less than a width of a body portion of the elastic arm.

7. The safety mechanism for a retaining needle according to claim 1, wherein the button has at least one driving arm extending radially, the driving arm has an inclined end and is disposed at an external side of the elastic arm; after the button is depressed, the inclined side of the inclined end of the driving arm gradually extrudes the elastic arm radially inwardly.

8. The safety mechanism for a retaining needle according to claim 7, wherein there are two driving arms.

9. The safety mechanism for a retaining needle according to claim 1, wherein the hollow handle comprises a cylindrical snap sleeve disposed inside the hollow handle; an edge of the snap sleeve extends to the distal side portion of the handle and the edge forms the snapping step, the elastic arm spreads radially outward and extends to the proximal direction from a distal side of the needle seat.

10. The safety mechanism for a safety mechanism according to claim 1, wherein the distal side portion of the hollow handle and the needle seat are made of a transparent material.

11. A retaining needle, the retaining needle comprising: a safety mechanism comprising: a snapping step disposed at an inner side of the hollow handle; at least one elastic arm radially spreading outward disposed on the needle seat, an end portion of the elastic arm has a snapping portion radially protruding outward, the snapping portion being engaged with the snapping step; and a button disposed on a distal side portion of the handle, the button, when being depressed, pushing the elastic arm along a radial inward direction, such that while the snapping portion of the elastic arm is disengaged from the snapping step, the needle seat and the puncture needle stretching outside of the handle are retracted into the hollow handle by virtue of vacuum within the hollow handle, wherein the button comprises a pressing portion and at least one extruding arm radially extending from the pressing portion, an end of the extruding arm having a thickened portion, wherein, when the button is not depressed, the extruding arm reaches into a gap between a body of the needle seat and the elastic arm spreading outward radially from the body and presses the elastic arm against the snapping step using the thickened portion, and wherein, after the button is depressed, the thickened portion of the extruding arm extends beyond the gap, not radially extruding the elastic arm outwardly anymore; a puncture needle fixed to a distal end of the needle seat; a catheter and a catheter hub disposed outside of the puncture.

12. The retaining needle according to claim 11, wherein the distal side portion of the hollow handle and the needle seat are made of a transparent material.

13. The retaining needle according to claim 11, wherein a vacuum sealing plug is provided between a base seat of the needle seat and a lumen of the hollow handle, so as to form a vacuum within the handle.

* * * * *